(12) United States Patent
Plaumann et al.

(10) Patent No.: US 9,833,387 B2
(45) Date of Patent: Dec. 5, 2017

(54) KIT AND METHOD FOR INDIRECT CHAIRSIDE PRODUCTION OF COMPOSITE INLAYS

(71) Applicant: VOCO GmbH, Cuxhaven (DE)

(72) Inventors: Manfred Thomas Plaumann, Cuxhaven (DE); Klaus-Peter Hoffmann, Cuxhaven (DE); Tobias Bloemker, Hamburg (DE); Alexander Willner, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 397 days.

(21) Appl. No.: 14/047,406

(22) Filed: Oct. 7, 2013

(65) Prior Publication Data

US 2014/0138864 A1 May 22, 2014

(51) Int. Cl.
- *B29C 39/02* (2006.01)
- *A61K 6/083* (2006.01)
- *A61K 6/00* (2006.01)
- *A61K 6/093* (2006.01)
- *B29C 39/00* (2006.01)

(52) U.S. Cl.
CPC ............ *A61K 6/083* (2013.01); *A61K 6/0008* (2013.01); *A61K 6/0052* (2013.01); *A61K 6/0073* (2013.01); *A61K 6/093* (2013.01); *B29C 39/003* (2013.01)

(58) Field of Classification Search
CPC ....................................................... A61K 6/083
See application file for complete search history.

(56) References Cited

U.S. PATENT DOCUMENTS

| | | | |
|---|---|---|---|
| 3,066,112 A | 11/1962 | Bowen | |
| 3,347,954 A | 10/1967 | Bredereck et al. | |
| 3,445,420 A | 5/1969 | Gust et al. | |
| 3,715,334 A | 2/1973 | Karstedt | |
| 3,775,352 A | 11/1973 | Leonard | |
| 3,814,730 A | 6/1974 | Karstedt | |
| 3,933,880 A | 1/1976 | Bergstrom et al. | |
| 3,989,667 A | 11/1976 | Lee et al. | |
| 4,110,184 A | 8/1978 | Dart et al. | |
| 4,115,346 A | 9/1978 | Gross et al. | |
| 4,323,348 A | 4/1982 | Schmitz-Josten et al. | |
| 4,575,805 A | 3/1986 | Moermann et al. | |
| 4,629,746 A * | 12/1986 | Michl | A61K 6/083 433/228.1 |
| 4,668,193 A * | 5/1987 | Burgess | A61O 5/002 433/159 |
| 4,744,827 A | 5/1988 | Winkel et al. | |
| 4,744,828 A | 5/1988 | Winkel et al. | |
| 4,772,530 A | 9/1988 | Gottschalk et al. | |
| 4,776,704 A | 10/1988 | Kopunek et al. | |
| 4,837,732 A | 6/1989 | Brandestini et al. | |
| 4,874,450 A | 10/1989 | Gottschalk | |
| 4,879,402 A | 11/1989 | Reiners et al. | |
| 4,954,414 A | 9/1990 | Adair et al. | |
| 5,055,372 A | 10/1991 | Shanklin et al. | |
| 5,057,393 A | 10/1991 | Shanklin et al. | |
| 5,063,257 A | 11/1991 | Akahane et al. | |
| 5,073,422 A * | 12/1991 | Konno | C08G 77/24 428/352 |
| 5,708,051 A | 1/1998 | Erdrich et al. | |
| 5,761,169 A | 6/1998 | Mine et al. | |
| 6,288,138 B1 | 9/2001 | Yamamoto et al. | |
| 6,361,925 B1 | 3/2002 | Leppard et al. | |
| 6,835,067 B2 | 12/2004 | Dorfman | |
| 6,919,386 B2 | 7/2005 | Wanek et al. | |
| 7,081,485 B2 | 7/2006 | Suh et al. | |
| 7,144,927 B1 | 12/2006 | Engelbrecht et al. | |
| 7,148,382 B2 | 12/2006 | Wolf et al. | |
| 7,488,762 B2 | 2/2009 | Takano et al. | |
| 7,601,767 B2 | 10/2009 | Ruppert et al. | |
| 7,879,924 B2 | 2/2011 | Torii et al. | |
| 2006/0004122 A1 * | 1/2006 | Hecht | A61K 6/0023 523/115 |
| 2007/0027229 A1 | 2/2007 | Moszner et al. | |
| 2008/0041520 A1 * | 2/2008 | Sun | A61K 6/0023 156/272.2 |
| 2008/0220396 A1 * | 9/2008 | Sun | A61K 6/0052 433/228.1 |
| 2010/0036015 A1 | 2/2010 | Luchterhandt et al. | |
| 2010/0190883 A1 | 7/2010 | Neffgen et al. | |
| 2011/0110998 A1 | 5/2011 | Marquais-Bienewald et al. | |
| 2012/0115108 A1 * | 5/2012 | Blomker | A61K 6/0023 433/217.1 |
| 2012/0196249 A1 | 8/2012 | Maletz et al. | |
| 2014/0228473 A1 * | 8/2014 | Osswald | A61K 6/10 523/109 |

FOREIGN PATENT DOCUMENTS

| | | | |
|---|---|---|---|
| DE | 1495520 A1 | 4/1969 | |
| DE | 2200021 A1 | 7/1973 | |

(Continued)

OTHER PUBLICATIONS

Kim, et al., Dental Materials, 2004, vol. 20, p. 88-95.

(Continued)

*Primary Examiner* — Ryan Ochylski
(74) *Attorney, Agent, or Firm* — Armstrong Teasdale LLP

(57) ABSTRACT

The present invention relates to a kit for indirect production of composite inlays, comprising a polymerizable material for production of a dental model, a polymerizable material for production of an inlay, a polymerizable material for luting of a crosslinked and non-sand-blasted, non-silanized, non-etched, non-primed and non-roughened composite inlay, the surfaces of which have been fully polymerized, in the cavity. Also disclosed is a polymerizable material for increasing the bond strength between the polymerizable material for luting of a crosslinked non-sand-blasted, non-silanized, non-etched, non-primed and non-roughened composite inlay, the surfaces of which have been fully polymerized, in the cavity, and the hard substance of the tooth, and an acid solution for surface etching of the hard substance of the tooth. The invention further relates to methods for producing a composite inlay.

20 Claims, No Drawings

(56) References Cited

FOREIGN PATENT DOCUMENTS

| | | |
|---|---|---|
| DE | 2419887 A1 | 11/1974 |
| DE | 2406557 A1 | 8/1975 |
| DE | 2816823 A1 | 10/1978 |
| DE | 2931926 A1 | 2/1981 |
| DE | 3236026 A1 | 3/1984 |
| DE | 3522005 A1 | 1/1987 |
| DE | 3522006 A1 | 1/1987 |
| DE | 3703080 A1 | 1/1988 |
| DE | 3703130 A1 | 1/1988 |
| DE | 3707908 A1 | 3/1988 |
| DE | 3819777 A1 | 12/1989 |
| DE | 4339399 A1 | 5/1995 |
| DE | 3941629 C2 | 11/1995 |
| DE | 4133494 C2 | 3/1996 |
| DE | 4446033 A1 | 6/1996 |
| DE | 19508586 C2 | 9/1996 |
| DE | 3801511 C2 | 11/1996 |
| DE | 19708294 A1 | 9/1997 |
| DE | 19701599 A1 | 7/1998 |
| DE | 19742980 A1 | 4/1999 |
| DE | 19908977 C1 | 5/2000 |
| DE | 19905093 A1 | 8/2000 |
| DE | 10001747 A1 | 7/2001 |
| DE | 10119831 A1 | 10/2002 |
| DE | 4231579 C2 | 11/2002 |
| DE | 10235990 A1 | 2/2004 |
| DE | 10339912 A1 | 3/2005 |
| DE | 69922413 T2 | 11/2005 |
| DE | 60300415 T2 | 3/2006 |
| DE | 60116142 T2 | 7/2006 |
| DE | 102005021332 B4 | 11/2006 |
| DE | 19753456 B4 | 1/2007 |
| DE | 102006019092 A1 | 3/2007 |
| DE | 60029481 T2 | 7/2007 |
| DE | 69935794 T2 | 12/2007 |
| DE | 102006050153 A1 | 5/2008 |
| DE | 112006001049 T5 | 12/2008 |
| DE | 102007050763 A1 | 4/2009 |
| DE | 102009006173 A1 | 7/2010 |
| DE | 102011003289 A1 | 7/2010 |
| DE | WO 2013025494 A1 * | 2/2013 ............... A61K 6/10 |
| EP | 0007508 A2 | 2/1980 |
| EP | 0023686 A2 | 2/1981 |
| EP | 0047902 A2 | 3/1982 |
| EP | 0049631 A1 | 4/1982 |
| EP | 0059451 A1 | 9/1982 |
| EP | 0057474 B1 | 10/1984 |
| EP | 0073413 B1 | 12/1984 |
| EP | 0173567 A1 | 3/1986 |
| EP | 0064834 B1 | 7/1987 |
| EP | 0184095 B1 | 7/1989 |
| EP | 0185613 B1 | 1/1991 |
| EP | 0262629 B1 | 4/1991 |
| EP | 0486774 A1 | 5/1992 |
| EP | 0366977 B1 | 3/1993 |
| EP | 0948955 A1 | 10/1999 |
| EP | 0980682 A1 | 2/2000 |
| EP | 0682033 B1 | 9/2000 |
| EP | 0450624 B1 | 9/2001 |
| EP | 0948955 B1 | 9/2003 |
| EP | 0980682 B1 | 11/2003 |
| EP | 0783880 B1 | 8/2004 |
| EP | 1018973 B1 | 12/2004 |
| EP | 1563821 A1 | 8/2005 |
| EP | 1236459 B1 | 11/2005 |
| EP | 1839640 A2 | 10/2007 |
| EP | 1685182 B1 | 12/2007 |
| EP | 1159281 B1 | 1/2008 |
| EP | 1502569 B1 | 12/2008 |
| EP | 2070935 A1 | 6/2009 |
| EP | 1773281 B1 | 11/2009 |
| EP | 1721949 B1 | 6/2010 |
| EP | 1457167 B1 | 8/2010 |
| EP | 1765265 B1 | 10/2010 |
| EP | 2034946 B1 | 10/2010 |
| EP | 1377628 B1 | 2/2011 |
| EP | 1874847 B1 | 2/2011 |
| EP | 1871333 B1 | 10/2011 |
| EP | 2004131 B1 | 10/2011 |
| EP | 2239275 B1 | 11/2011 |
| EP | 2450025 A1 | 5/2012 |
| EP | 2436668 B1 | 9/2012 |
| JP | H01121370 A | 5/1989 |
| JP | H07206740 A | 8/1995 |
| JP | H07206741 A | 8/1995 |
| JP | 2006299202 A | 11/2006 |
| WO | 0192374 A1 | 12/2001 |
| WO | 02085974 A1 | 10/2002 |
| WO | 02092021 A1 | 11/2002 |
| WO | 02092023 A1 | 11/2002 |
| WO | 2005084611 A1 | 9/2005 |
| WO | 2006005363 A1 | 1/2006 |
| WO | 2006005366 A1 | 1/2006 |
| WO | 2006005368 A1 | 1/2006 |

OTHER PUBLICATIONS

Mechanical Rubber, "Durometer Conversion Chart, Approximate Hardness Value," available at https://mechanicalrubber.com/elastomericsolutions/wp-content/uploads/2013/08/Durometer-Conversion-Table.pdf accessed on Apr. 3, 2017.

Sciencelab.com, Inc. "Material Safety Data Sheet, Methyl Acetate MSDS," CAS#: 79-20-9, available at http://www.sciencelab.com/msds.php?msdsId=9927568 (Last updated May 21, 2013).

European Search Report Issued for Application No. EP13004610 dated Dec. 9, 2016.

German Search Report Issued for Application No. DE102013008176.9, dated May 14, 2013.

* cited by examiner

KIT AND METHOD FOR INDIRECT CHAIRSIDE PRODUCTION OF COMPOSITE INLAYS

CROSS-REFERENCE TO RELATED APPLICATIONS

This application claims priority to German Patent Application No. 102012019514.1, filed Oct. 5, 2012, which is herein incorporated by reference in its entirety.

The present invention relates to a kit for indirect production of composite inlays, comprising a polymerizable material for production of a dental model, a polymerizable material for production of an inlay, a polymerizable material for luting of a crosslinked and non-sand-blasted, non-silanized, non-etched, non-primed and non-roughened composite inlay, the surfaces of which have been fully polymerized, in the cavity, and optionally, if, for example, the polymerizable material for luting of a crosslinked and non-sand-blasted, non-silanized, non-etched, non-primed and non-roughened composite inlay, the surfaces of which have been fully polymerized, is not self-adhesive in the cavity, a polymerizable material for increasing the bond strength between the polymerizable material for luting of a crosslinked, non-sand-blasted, non-silanized, non-etched, non-primed and non-roughened composite inlay, the surfaces of which have been fully polymerized, in the cavity and the hard substance of the tooth, and likewise optionally, in the case of a polymerized material for increasing the bond strength between the hard substance of the tooth and luting of material, an acid solution for surface etching of the hard substance of the tooth. The invention further relates to methods for producing a composite inlay.

"(Meth)acryloyl" in the context of the present text should be understood to mean both acryloyl and methacryloyl.

The dental literature discloses a multitude of methods for treatment of cavities in previously treated teeth. For a long time, metals or alloys were considered to be the gold standard as materials of choice for treatment of large- or multisurface cavities. For instance, amalgams are still available to the dentist today as filling materials. Particularly in the case of relatively large restorations, however, inlays or onlays based on noble metals are also frequently used. In this case, the dentist first makes an impression of the dental situation after preparation and closes the cavity temporarily. Subsequently, a dental technician in a laboratory produces a tooth restoration which is then introduced into the patient's cavity during a further sitting. In spite of the good mechanical properties and satisfactory qualities of the filling margins, particularly when gold is used, this having very good processability because of its ductility, the metal-based restorations lack esthetic appeal, which is becoming ever more important.

Because of the patients' wish for esthetic dental treatment, including in the posterior region, and advances in the development of dental restoration polymers, these have become ever more important. In this context, particularly filling materials based on (meth)acrylates have become established, these either self-curing through redox reactions or being cured by radiation after introduction into the cavity.

A problem with the use of (meth)acrylate-based filling polymers which are polymerized directly in large- or multisurface cavities, however, is the intrinsic polymerization shrinkage. The phenomenon of polymerization shrinkage corresponds to a change in density which occurs during and after the crosslinking. This has essentially two causes. Firstly, in the course of polymerization, the monomer units approach one another from a van der Waals distance to the distance of a covalent bond, and, secondly, the packing density of the polymer chains is higher than the packing density of the monomers. The shrinkage (volume contraction) of the reactive resin material depends primarily on the number of functional groups which have reacted. Shrinkage occurs both in the liquid state, i.e. right at the start of the polymerization, and during and after gelation. The total shrinkage includes a physical component and a chemical component. While physical shrinkage is directional and proceeds three-dimensionally from the outer regions of the polymer inward with the temperature gradient to the middle of the curing molding material, the chemical component is non-directional and results solely from the polymer formation. At the start of the polymerization, the volume contraction can still be compensated for by inflow of the material. But within a short time, the polymer network has built up to such an extent that the gel point has been attained, the mobility of the monomers is restricted and inflow of the material becomes impossible. In this state, inner stresses disadvantageously arise in the material, and these, in the case of use as a dental filling material, either lead to detachment from the cavity walls and hence to marginal gap formation, or weaken the material through the formation of volume defects.

The monomer most frequently used to date in the dental industry is 2,2-bis[4-(2-hydroxy-3-methacryloyloxypropoxy)phenyl)propane described in U.S. Pat. No. 3,066,112 A by Bowen, or bis-GMA for short. Bis-GMA, synthesized from 2 mol of glycidyl methacrylate and one mole of bisphenol A contains, at each of its two ends, a terminal vinyl group which polymerizes rapidly in a free-radical reaction and gives rise to a crosslinked polymer. The chemical structure of bis-GMA has some peculiarities. For instance, the two aromatic rings lead to a high refractive index, whereas the hydroxyl groups in the side chains lead to formation of superstructures, and the methyl groups in the propane radical make free rotation of the molecule impossible. These structural features of bis-GMA enable the formation of what is called a superstructure based on the hydrogen bonds in the polymer, the superstructures being extremely tightly packed because of the rigid molecular conformation. This leads to particularly good mechanical properties of the material. However, the hydroxyl groups and the high molecular weight also lead to a very high viscosity of the bis-GMA.

Therefore, conventional dental composite materials comprise what are called low molecular weight reactive diluents which lower the viscosity and ensure the processability of the composite material. Conventional dental composite materials thus consist of a voluminous monomer such as, in particular, bis-GMA, and low molecular weight monomers (reactive diluents), for example triethylene glycol dimethacrylate (TEDMA), and customary fillers, polymerization initiators and additives.

There have additionally been past proposals of monomer systems in which the volume contraction was to be compensated for by means of ring-opening reactions. Other developments utilize a cationic ring-opening polymerization rather than a free-radical addition polymerization. In addition, liquid-crystalline monomers, dendritic monomers or organic-inorganic hybrid materials such as the ormocers (organically modified ceramics) have been tested. In terms of concept, attempts have thus been made to overcome the volume contraction through a shift in the balance between broken and newly formed covalent bonds, or through differences in the packing density between liquid and solid phases.

Likewise already known is the use of free-radically polymerizable methacrylic or acrylic esters with a tricyclo [5.2.1.0$^{2,6}$]decane (TCD) structural element for production of low shrinkage dental materials.

Dental composite materials containing free-radically polymerizable methacrylic or acrylic esters with a tricyclo [5.2.1.0$^{2,6}$]decane structural element are specified, inter alia, in the following publications: DE 28 16 823 A1, DE 24 19 887 A1, DE 24 06 557 A1, DE 29 31 926 A1, DE 35 22 005 A1, DE 35 22 006 A1, DE 37 03 080 A1, DE 37 03 130 A1, DE 37 07 908 A1, DE 38 19 777 A1, DE 197 01 599 A1, DE 699 35 794 T2.

Documents DE 22 00 021 A1, EP 0 023 686 A2, EP 0 049 631 A1, JP 07206740 A, JP 07206741 A and JP 01121370 A likewise disclose free-radically polymerizable methacrylic or acrylic esters with a tricyclo[5.2.1.0$^{2,6}$]decane structural element.

DE 10 2005 021 332 B4 also describes composite materials which are said to have low shrinkage capacity.

As well as the concept of direct filling introduction, some indirect methods are also performed in practice. In this case, an impression is first produced by the dentist, which is then applied to a plaster model in the laboratory. A restoration is then manufactured thereon, and this is bonded into the temporarily treated cavity by the dentist in a further sitting.

In the last few years, technical advances have provided computer-animated machinery capable of producing prostheses with minimal human labor and drastically lower working time. This is frequently referred to as "digital dentistry", in which computer automation is combined with optics, digitalization equipment, CAD-CAM (Computer-Aided Design/Computer-Aided Machining) and mechanical machining tools. Examples of such a computer-assisted machining system include the CEREC 2™ machine supplied by Siemens (available from Sirona Dental Systems; Bensheim, Germany), VITA CELAY™ (available from Vita Zahnfabrik; Bad Sackingen, Germany), PRO-CAM™ (Intra-Tech Dental Products, Dallas, Tex., USA) and PRO-CERA ALLCERAM™ (available from Nobel Biocare USA, Inc.; Westmont, Ill., USA). U.S. Pat. Nos. 4,837,732 A, 4,575,805 A and 4,776,704 A also disclose the technology of computer-assisted machining systems for production of dental prostheses. These machines produce dental prostheses by cutting, machining and grinding the almost exact shape and morphology of a required restoration with high speed and less labor than conventional manual processes.

Corresponding mill blanks are disclosed, inter alia, in DE 699 22 413 12.

The CAD/CAN methods mentioned, however, have the disadvantage that the dentist or the dental laboratory first has to purchase scanning and machining systems, which is associated with very high capital costs.

As well as the indirect method described, via work in a dental laboratory or the use of CAD/CAM-assisted machining systems, the literature also describes methods in which the restoration, in one sitting, is first produced intra- or extraorally, optionally polymerized and only then bonded within the cavity.

EP 0 185 613 B1 describes a process in which the cavity is first provided with an insulation layer. Subsequently, a composite material is introduced and polymerized in the cavity, and the finished restoration is removed again. After cleaning, the finished workpiece is cemented in. This method is problematic when the cavity preparation leaves what is called an undercut. This enables the introduction of the unpolymerized filling material, but prevents the removal subsequently necessary.

EP 1 018 973 B1 and EP 1 457 167 B1 describe processes in which several impressions are produced and a polymerizable material, which subsequently constitutes the restoration, is introduced between a preoperative and postoperative impression. Overall, four different polyvinylsilicone materials are used in the methods. The composite material used for the dental restoration is subsequently cured with light and/or heat in a specific apparatus. Overall, in the method described, it is necessary to wait for four different setting times for the polyvinylsilicone materials, which makes the method very time-consuming.

Already prefabricated inlays made from acrylates, porcelain or acrylate-ceramic composite materials are used in U.S. Pat. No. 6,835,067 B2 for treatment of MO (mesial-occlusal) and MOD (mesial-occlusal-distal) cavities. Inlays of various geometric basic forms for dental restorations are assembled in one kit. In addition, the inlays have a tab for trying-in. The inlays are fitted to the current cavity situation before being inserted, but are not produced individually, and hence bonding joints of different shape between inlay and tooth substance are to be expected.

For luting of tooth restorations in the cavity, luting cements are typically used. These are known for a multitude of tooth restoration materials, such as metals, ceramics or plastics, and are described, inter alia, in EP 0 486 774 A1, EP 0 064 834 B1 or EP 2 450 025 A1.

In order to achieve a sufficiently high bond strength between the tooth restoration and the luting cement, the tooth restoration is typically pretreated in various ways. These pretreatments include the methods of silanizing, silicatizing, blasting and chemical conditioning, enumerated in DE 199 08 977 C1. These methods can be employed not just alternatively but also successively. Chemical conditioning in the context of this invention encompasses the etching of the surface of the tooth restoration with acid and "priming". The term "priming" is understood by the person skilled in the art in the field of dental chemistry to mean an operation in which the surface of a substrate to be bonded is pretreated such that a subsequent bonding step can be executed more effectively. A "primer" corresponds to a chemical composition, usually based on an unreactive solvent, which additionally always contain (usually hydrophilic) monomers crosslinkable with an adhesive and adhesion-promoting compounds.

The activation of the surfaces of the dental restoration serves for the cohesive, permanent, stress-stable bonding of the dental restoration to the dental polymer.

Even when luting cements available on the market are used, such as Multilink (Ivoclar Vivadent, Liechtenstein) or RelyX™ Unicem 2 (3M Deutschland GmbH, Neuss), a respective pretreatment is specified for various dental restoration materials. In the case of dental restorations based on methacrylate-based composite materials, this is typically sand-blasting or jet-blasting with aluminum oxide or another kind of mechanical roughening. Without this pretreatment, a sufficient adhesive bond between luting cement and composite restoration is not achieved. This necessary pretreatment is typically performed in the dental laboratory in which the restoration has been produced. Corresponding equipment is not available in all dental practices.

In the case of mechanical pretreatment with a customary treatment instrument, for instance a finisher or diamond polisher, it is not possible to ensure that all regions, some of them very small, in the restoration are sufficiently roughened. Moreover, the accuracy of fit of the dental restoration decreases as a result of the material removal, and an unfavorably large joint arises.

DE 43 39 399 A1 describes inserts having incompletely polymerized surfaces after production. These so-called smear layers do not need any further surface treatment, since they ensure excellent adhesion to the luting of composite per se. In order not to destroy the smear layer after the production of the inserts, it is stated that the inserts should be handled cautiously with tweezers.

To check the fitting accuracy of an individually manufactured inlay, however, it is generally introduced into the cavity to test the fit before bonding, and then the suitability of the inlay is checked either visually or using special control silicone. For hygienic reasons alone, it is vital that the inlay, after checking the fit and before being bonded, can be disinfected and freed of saliva, blood and other residues. During this cleaning, any inhibited smear layer is removed, and so the inserts disclosed in DE 43 39 399 A1 do not allow checking for fit and cleaning.

The cleaning can be effected by mechanical wiping, spraying with water and/or cleaning with alcohols (preferably ethanol, n-propanol, isopropanol) or other solvents. The use of specific alcoholic solutions additionally makes it possible to achieve disinfection.

In this case, it is possible to add to the solutions additives such as quaternary ammonium compounds, for example benzalkonium chloride, aldehydes, guanidines, for example chlorhexidine or alexidine, mecetronium etilsulfate, alkylamines, triclosan, carolactone, alkyl- and acylpyridinium derivatives, silanols, chitosan, glycerol phosphate derivatives, bispyridines such as octenidine dihydrochloride, pyrimidines such as hexetidine, iminopyridinium derivatives, octenidine salt, dequalinium salt, sanguinarine, Akacid® or cation-active compounds such as cetylpyridinium chloride.

Ionic and/or nonionic surfactants can likewise be added to the solutions in order to increase the disinfecting properties.

In the field of dental restorations, there is a constant need for economic solutions which enable the best treatment of a cavity qualitatively possible within a period appropriate to patients and dentists. In this context, particularly the rapid treatment of a cavity with a long-lived and reliable restoration in only one sitting is of great interest.

It is therefore a primary object of the present invention to provide a kit which enables simple and high-quality production of inlays by indirect chairside manufacture, which can be cleaned before bonding or after checking for size, and additionally have high bond strengths to luting cements. The inlays produced with the inventive kit preferably have the feature that the material parameters of the individual constituents are matched to one another such that marginal gap-free bonding of the composite inlays with the tooth substance is possible with high bond strength.

This object is achieved by an inventive kit for restoration of a tooth cavity, comprising
A. a polymerizable material for production of a dental model, comprising either
　A.a. addition-crosslinking silicones
　or
　A.b. cationically curable polyethers,
B. a polymerizable material for production of a composite inlay, comprising
　B.a. a total amount of fillers in the range from more than 75 to 95% by weight, based on the total mass of the polymerizable material for production of a composite inlay B,
　B.b. a total amount of polymerizable monomers or monomer mixtures in the range from 3 to less than 25% by weight, based on the total mass of the polymerizable material for production of a composite inlay B, wherein the total amount of polymerizable monomers is selected from the group comprising carbosilanes, monomers which cure via ring-opening metathesis polymerization, and dental (meth)acrylate monomers,
　B.c. one or more photoinitiator(s) and/or initiator(s) for chemical curing,
　and optionally
　B.d. one or more other additive(s),
C. a polymerizable material for luting of a composite inlay in the cavity, comprising
　C.a. a total amount of fillers of more than 40 to 80% by weight based on the total mass of the polymerizable material for luting of a composite inlay in the cavity C,
　C.b. 16.8 to less than 60% by weight of a total amount of one, two or more polymerizable monomers, based on the total mass of the polymerizable material for luting of a composite inlay in the cavity C, the one, two or more polymerizable monomers being selected from the group comprising carbosilanes, monomers which cure via ring-opening metathesis polymerization, and dental (meth)acrylate monomers,
　C.c. 0.1 to 10% by weight of one or more photoinitiator(s) and/or initiator(s) for chemical curing, based on the total mass of the polymerizable material for luting of a composite inlay in the cavity C,
　C.d. optionally one or more adhesion monomer(s) other than constituent C.b, preferably containing a phosphoric acid radical, a diphosphoric acid radical, a phosphonic acid radical, a thiophosphoric acid radical or a sulfonic acid radical in a proportion of less than 35% by weight, based on the total mass of the polymerizable material for luting of the composite inlay in the cavity, and
　C.e. polymerization inhibitors,
　C.f. less than 3% by weight of additives, based on the total mass of the polymerizable material, for luting of a composite inlay in the cavity C,
and optionally
D. a polymerizable material for establishment of a bond between the hard substance of the tooth and luting cement, comprising
　D.a. one or more adhesion monomer(s), preferably light-polymerizable adhesion monomers, containing a phosphoric acid radical, a diphosphoric acid radical, a phosphonic acid radical, a thiophosphoric acid radical or a sulfonic acid radical,
　D.b. acid group-free monomers copolymerizable with constituent D.a. other than constituent D.a., preferably light-polymerizable monomers,
　D.c. one or more fillers, preferably one or more nanoscale fillers,
　D.d. one or more photoinitiator(s) and/or initiator(s) for chemical curing,
　D.e. polymerization inhibitors, and optionally
　D.f. solvents and optionally
　D.g. additives,
and optionally
E. an acid solution for etching the hard substance of the tooth,
wherein the composite inlay which has not been sandblasted, nor silanized, nor etched, nor primed, nor roughened, before being bonded into the tooth cavity and is obtainable by curing the polymerizable material for production of a composite inlay has fully polymerized surfaces, and the deformation under pressure of the polymerizable material for production of a dental model, measured to ISO 4823, is not more than 3.5%, and the polymerization shrinkage of the polymerizable material for production of a composite inlay, measured by the bonded-disc method, is not more than 2.0%, and wherein the adhesive force between the composite inlay and the luting cement, measured by the VOCO test method, is at least 8 MPa.

More particularly, this object is achieved by an inventive kit for restoration of a tooth cavity, wherein A.a. comprises
- A.a.1. 10-40% by weight of polysiloxanes comprising polyatomic crosslinkable groups,
- A.a.2. 2-10% by weight of organo-hydropolysiloxanes,
- A.a.3. 0.01-1% by weight of catalyst,
- A.a.4. 50-90% by weight of fillers and optionally
- A.a.5. additives,
- where the percentages by weight are based on the total mass of the addition-crosslinking silicones, or A.b. comprises
- A.b.1. 30-90% by weight of aziridine group-bearing copolymers,
- A.b.2. 1-10% by weight of starter substances suitable for bringing about the curing of the aziridine group-bearing copolymers,
- A.b.3. 3-45% by weight of fillers,
- A.b.4. 2-85% by weight of additives,
- where the percentages by weight are based on the total mass of the cationically curable polyethers, and B.a. comprises
- B.a.1. a total amount in the range from 2 to 30% by weight of organically surface-modified nanoparticles having a mean primary particle size less than 200 nm and
- B.a.2. a total amount in the range from 45 to less than 85% by weight of microparticles having a mean particle size in the range from 0.4 µm to 10 µm, and optionally
- B.a.3. further fillers other than B.a.1 and B.a.2,
- where the percentages by weight for components B.a.1 and B.a.2 are based on the total mass of the polymerizable material for production of a composite inlay B, and C.a. comprises
- C.a.1. one or more fractions of microparticles having a mean particle size of 0.4 µm to 10 µm,
- C.a.2. nanoscale, preferably surface-modified, solid particles having a primary particle size of not more than 200 nm, preferably not more than 100 nm and especially not more than 70 nm.

In addition, the object is achieved by methods for production of a composite inlay, characterized in that it comprises the following steps:

casting an impression of a tooth cavity with a polymerizable material for production of a dental model A,
polymerizing the polymerizable material for production of a dental model A,
applying a polymerizable material for production of a composite inlay B to the dental model, formed by the polymerized material for production of a dental model A,
forming the polymerizable material for production of a composite inlay B into the form of an inlay which fills the tooth cavity of which an impression has been taken,
polymerizing the polymerizable material for production of a composite inlay B
optionally repeating the application, forming and polymerizing of the polymerizable material for production of a composite inlay B if the inlay is to be built up layer by layer,
withdrawing the polymerized composite inlay produced from the dental model,
removing the inhibited or incompletely polymerized layers of the composite inlay by wiping-off and application of alcohol or alcoholic or aqueous disinfection solutions.

The object is achieved particularly efficiently by a method for producing a composite inlay as described above, wherein the polymerizable material for production of a dental model comprises A. either
A.a. addition-crosslinking silicones comprising
- A.a.1. 10-40% by weight of polysiloxanes comprising polyatomic crosslinkable groups,
- A.a.2. 2-10% by weight of organo-hydropolysiloxanes,
- A.a.3. 0.01-1% by weight of catalyst,
- A.a.4. 50-90% by weight of fillers and optionally
- A.a.5. additives,
- where the percentages by weight are based on the total mass of the addition-crosslinking silicones, or A.b. cationically curable polyethers comprising
- A.b.1. 30-90% by weight of aziridine group-bearing copolymers,
- A.b.2. 1-10% by weight of starter substances suitable for bringing about the curing of the aziridine group-bearing copolymers,
- A.b.3. 3-45% by weight of fillers,
- A.b.4. 2-85% by weight of additives,
- where the percentages by weight are based on the total mass of the cationically curable polyethers, and wherein, preferably, from the polymerizable material for production of a dental model A.a, component A.a.1 comprises a mixture of two linear vinylmethylsiloxanes, wherein the dynamic viscosity, measured to DIN 53018 at 25° C., of one linear vinylmethylsiloxane having terminal vinyl groups is in the range from 200 mPas up to and including 2500 mPas, and that of the second linear vinylmethylsiloxane likewise having terminal vinyl groups is within the range from greater than 2500 mPas up to and including 65 000 mPas, and wherein the weight ratio of the low-viscosity to the high-viscosity vinylmethylsiloxane is 6:1 to 1:4, wherein, preferably, component A.a.2 has two to three Si—H bonds per molecule, wherein, preferably, component A.a.3 is a platinum catalyst, more preferably the Karstedt catalyst, wherein component A.a.4 is selected from the group comprising cristobalite, silicates, montmorillonites, bentonites, metal oxide powders, titanium dioxide, gypsum, inorganic salts, glass, crystalline and amorphous silica, quartz, diatomaceous earth, and nanoscale particles in the form of non-aggregated and non-agglomerated particles, especially nanoscale silicas,
wherein the fillers are in surface-treated form,
wherein component A.a.5 comprises
one or more inhibitor(s) in amounts of 0.001-0.15% by weight, based on the total mass of component A.a,
one or more stabilizer(s) in amounts of 0.1 to 5% by weight, based on the total mass of component A.a,
one or more rheology modifiers in amounts of 1 to 10% by weight, based on the total mass of component A.a, and optionally
dyes, wetting agents and antioxidants,
wherein the addition-crosslinking silicone A.a is a two-component system composed of base paste and catalyst paste,
wherein base paste and catalyst paste are present in a volume ratio of 10:1 to 1:10 and
wherein A.a has a processing time at 23° C. of more than 30 seconds, preferably more than 45 seconds, and a setting time at 30° C. of less than 7 minutes, preferably less than 5 minutes, and
wherein the deformation under pressure of the addition-crosslinked silicone A.a measured to ISO 4823 is not more than 3.5% and the Shore D hardness, determined to DIN 53505, is in the range between 25 and 85,
and wherein the polymerizable material for production of a composite inlay
B. comprises
B.a. a total amount of fillers in the range from more than 75 to 95% by weight, based on the total mass of the polymerizable material for production of a composite inlay B, wherein the total amount of fillers is a mixture of fillers comprising
B.a.1. a total amount in the range from 2 to 30% by weight of organically surface-modified nanoparticles having a mean primary particle size less than 200 nm and
B.a.2. a total amount in the range from 45 to less than 85% by weight of microparticles having a mean particle size in the range from 0.4 µm to 10 µm, and
B.a.3. optionally further fillers other than B.a.1 and B.a.2, where the percentages by weight for components B.a.1 and B.a.2 are based on the total mass of the polymerizable material for production of a composite inlay B, and
wherein the microparticles of component B.a.2 are selected from the group consisting of materials based on silicon dioxide, zirconium dioxide and/or titanium dioxide, and also mixed oxides, fumed silicas or precipitated silicas, quartz glass ceramics or dental glass powders, barium glasses or strontium glasses, fluoride ion-releasing glasses, oxides of aluminum or silicon, zeolites, apatites, zirconium silicates, sparingly soluble metal salts and X-ray-opaque fillers, and
wherein the fillers of component B.a.3 are preferably selected from the group consisting of fibers, finely divided chip polymers or bead polymers, and
wherein the organically surface-modified nanoparticles of component B.a.1 are oxides or mixed oxides selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof,
wherein the surface-modified nanoparticles are silanized and are preferably in monodisperse form, and
B.b. a total amount of polymerizable monomers or monomer mixtures in the range from 3 to 25% by weight, based on the total mass of the polymerizable material for production of a composite inlay, wherein the total amount of polymerizable monomer is selected from the group comprising carbosilanes, monomers which cure via ring-opening metathesis polymerization, and dental (meth)acrylate monomers, wherein the dental (meth)acrylate monomers in the polymerizable material for production of a composite inlay B are selected from the group comprising
B.b.1 comprising one, two or more monomers selected from the group comprising 2,2-bis[4-(2-hydroxy-3-(meth)acryloyloxypropoxy)phenyl) propane (bis-GMS), bisphenol A glycidyl(meth)acrylate, bisphenol B glycidyl(meth)acrylate, bisphenol C glycidyl(meth)acrylate, bisphenol F glycidyl(meth)acrylate, alkoxylated bisphenol A glycidyl(meth)acrylate, ethoxylated bisphenol A di(meth)acrylate, 7,7,9-trimethyl-4,13-dioxo-5,12-diazahexadecane 1,16-dioxydi(meth)acrylate (UDMA), compounds which are free-radically polymerizable via (meth)acrylate groups and comprise a polyalicyclic structural element, and ormocers
and
B.b.2 comprising one, two or more further free-radically polymerizable monomer(s) from the group consisting of (meth)acrylates which are not part of the list described for B.b.1,
and wherein B.b.2 is selected from the group comprising ethylene glycol di(meth)acrylate (EGDMA), 1,6-hexanediol di(meth)acrylate (HEDMA), triethylene glycol di(meth)acrylate (TEDMA), 1,12-dodecanediol di(meth)acrylate (DODMA), polyethylene glycol di(meth)acrylate (PEGDMA), butanediol di(meth)acrylate, tetraethylene glycol di(meth)acrylate, neopentyl glycol di(meth)acrylate, 2-hydroxypropyl 1,3-di(meth)acrylate, 3-hydroxypropyl 1,2-di(meth)acrylate, pentaerythritol di(meth)acrylate, glyceryl di(meth)acrylate, 2-hydroxyethyl(meth)acrylate, 2-hydroxypropyl(meth)-acrylate, 3-hydroxypropyl(meth)acrylate, 1,2-dihydroxypropyl(meth)acrylate, 1,3-dihydroxypropyl(meth)acrylate, 2,3-di-hydroxypropyl(meth)acrylate,
2-hydroxypropyl 1,3-di(meth)acrylate and 3-hydroxypropyl 1,2-di(meth)acrylate, 2-(meth)acryloyloxyethyl dihydrogenphosphate, bis[2-(meth)acryloyloxyethyl]hydrogenphosphate, 2-(meth)acryloyloxy-ethylphenyl hydrogenphosphate, 6-(meth)acryloyloxyhexyl dihydrogenphosphate, 10-(meth)acryloyloxydecyl dihydrogenphosphate (MDP), 1,3-di(meth)acryloyloxypropane 2-dihydrogenphosphate, 1,3-di(meth)acryloyloxypropane 2-phenyl hydrogenphosphate and bis[5-(2-(meth)acryloyloxyethoxycarbonyl)heptyl] hydrogenphosphate, 4-(meth)acryloyloxy-ethyltrimellitic acid (4-MET), 4-(meth)acryloyloxyethyltrimellitic anhydride (4-META), 4-(meth)acryloyloxy-decyltrimellitic acid, 4-(meth)acryloyl-oxydecyltrimellitic anhydride, 11-(meth)acryloyloxy-1,1-undecanedi-carboxylic acid, 1,4-di(meth)acryloyl-oxypyromellitic acid, 2-(meth)acryloyl-oxyethylmaleic acid, 2-(meth)acryloyloxyethylphthalic acid and 2-(meth)acryloyloxyethylhexahydrophthalic acid, and polymerizable phosphoric esters bearing a polyalicyclic structural element, and wherein the ratio of the mass of component B.b.1 to the mass of component B.b.2 is in the range from 10:1 to 1:10, and B.c. one or more photoinitiators and/or initiators for chemical curing, wherein the photoinitiators are selected from the group consisting of alpha-diketones, benzoin alkyl ethers, thioxanthones, benzophenones, acylphosphine oxides, acetophenones, ketals, titanocenes, sensitizing dyes and borate salts, and the initiators of chemical curing are selected from the group consisting of peroxides, barbituric acids, barbituric acid derivatives, salts of barbituric acid, salts of a barbituric acid derivative, malonyl-sulfamides and sulfur compounds in the +2 or +4 oxidation state, and wherein the photoinitiators are used individually or in mixtures, and the photoinitiators used individually or in mixtures are used in combination with accelerators, wherein the accelerators provided are amines, aldehydes, sulfur compounds, barbituric acids and tin compounds, and wherein the chemical catalysts are used in combination with redox partners and optionally with accelerators, and wherein the photoinitiators are optionally also used together with the catalysts of chemical curing, and wherein the photoinitiator preferably consists of a combination of camphorquinone/amine or of one or more phosphine oxides or of the combination of camphorquinone/amine/phosphine oxides, and the chemical catalyst preferably consists of a combination of peroxide/amine or of the barbituric acid/barbituric acid derivative/-salt of barbituric acid/salt of a barbituric acid derivative system and one or more heavy metal salt(s) and/or heavy metal complexes, wherein the heavy metal salt of the barbituric acid/barbituric acid derivative/salt of barbituric acid/salt of a barbituric acid derivative system is preferably selected from the group consisting of iron salt, copper salt or cobalt salt and copper acetylacetonate or the bis(1-phenylpentane-1,3-dionato)copper(II) complex, and wherein the barbituric acid/barbituric acid derivative/salt of a barbituric acid/salt of a barbituric acid derivative system preferably additionally comprises ionically bonded halogens or pseudohalogens, and wherein a peroxy compound as an oxidizing agent is optionally also added to the barbituric acid/barbituric acid derivative/-salt of barbituric acid/salt of a barbituric acid derivative system, and optionally one or more additives, and B.d. additives selected from the group comprising inhibitors, fluoride-releasing substances, UV absorbers, dyes and flavorings, wherein the inhibitors are selected from the group comprising hydroquinone monomethyl ether, phenols, phenothiazine, derivatives of phenothiazine, 2,3,6,6-tetramethylpiperidinyl-1-oxyl radicals, triphenylmethyl radicals, galvinoxyl radicals, 2,2-diphenyl-1-picrylhydrazyl radicals, tert-butylhydroxyanisole and 2,6-di-tert-butyl-4-methylphenol, and wherein the inhibited or incompletely polymerized layer of the composite inlay is removed by wiping-off and application of alcohols, preferably of ethanol, n-propanol and/or isopropanol, individually or in mixtures and/or by means of aqueous/alcoholic solutions optionally comprising antimicrobial and/or surface-active additives.

In the context of the invention, a polymerizable material for luting of an inlay is understood to mean a polymerizable material for luting of a non-sand-blasted, non-silanized, non-etched, non-primed and non-roughened composite inlay in a cavity. This polymerizable material for luting of a non-sand-blasted, non-silanized, non-etched, non-primed and non-roughened composite inlay in a cavity is also referred to as luting cement.

In the context of the invention, moreover, a polymerizable material for increasing the adhesion capacity between luting cement and the hard substance of the tooth is understood to mean a polymerizable material for increasing the adhesion capacity between the polymerizable material for luting of a non-sand-blasted, non-silanized, non-etched, non-primed and non-roughened composite inlay in a cavity and the hard substance of the tooth, which is used optionally, for example if the polymerizable material for luting of a non-sand-blasted, non-silanized, non-etched, non-primed and non-roughened composite inlay in a cavity is not self-adhesive.

It has been found that, surprisingly, the non-sand-blasted, non-silanized, non-etched, non-primed and non-roughened composite inlays which have fully polymerized surfaces and have been produced using the inventive kit, without pretreatment and after removal of any inhibited layers present, have bond strengths of >(i.e. more than) 8 MPa and regularly >15 MPa to the luting cement which is likewise described as a constituent of an inventive kit.

It has additionally been found that, surprisingly, the deformation under pressure of the polymerizable material for production of a dental model and the polymerization shrinkage of the polymerizable material for production of an inlay can be matched to one another such that the layer thickness of the polymerizable material for luting of an inlay, when an inlay produced from the polymerizable material for production of an inlay is inserted into the cavity, is such that the polymerizable material for luting of an inlay can exert an optimal bond strength and hence has high marginal integrity. This applies when the deformation under pressure of the polymerizable material for production of a dental model measured to ISO 4823 is <(i.e. less than) 3.5%, preferably <1.5% and more preferably <1.0%, and the polymerization shrinkage of the polymerizable material for production of the inlay measured by the bonded-disc method is not more than 2.0%, preferably not more than 1.8%.

If, for example, the polymerizable material for luting of an inlay is incapable of conditioning tooth substance, a polymerizable material which strengthens the bond between the polymerizable material for luting of an inlay and the tooth substance is additionally required.

Optionally, in the case of a polymerizable material for increasing the bond strength between the hard substance of the tooth and luting cement, an acid solution for surface etching of the hard substance of the tooth is also provided.

"Chairside" in the context of this application is understood to mean that the dentist or dental technician produces and definitively bonds in the final restoration during one sitting, i.e. during one patient visit, ideally within the period of the anesthesia for the preparation.

The word "indirectly" in the context of this application describes extraoral modeling, polymerization and production. The final elaboration of the restoration, more particularly the polishing and fitting of the restoration to the respective occlusion, can also be effected intraorally.

In the first step of the way described here of producing a composite inlay using the inventive kit, an impression (for example based on an alginate) of the dental situation after the preparation of the tooth or teeth to be treated is made with a curable composition for production of a dental model. By casting the impression made and subsequent polymerization, a positive model of the cavity situation is obtained. In order to make an exact model, the polymerizable material for production of a dental model should have a processing time of >(i.e. more than) 30 seconds, preferably >45 and more preferably >60 seconds. In addition, the consistency should be sufficiently thin to ensure high reproduction accuracy in the casting of the impression.

As well as a sufficient processing time, sufficiently low deformation under pressure is of crucial significance for the use of the polymerizable material for production of a dental model. Deformation under pressure is determined to ISO 4823 and at the end of the setting time. In order to ensure sufficiently rapid production of a tooth restoration during one sitting, the setting time of the polymerizable material for production of a dental model at 23° C. is <(i.e. less than) 7 min, preferably <5 min and more preferably <4 min. The deformation under pressure is <(i.e. less than) 3.5%, preferably <1.5% and more preferably <1.0%. In practice, the deformation under pressure corresponds to an inaccuracy in the restoration produced, which is caused by a deformation of the model material (formed by the polymerizable material for production of a dental model).

The polymerizable material for production of a dental model is selected from the group consisting of polyethers and addition-crosslinking silicones. Preferably, the polymerizable material for production of a dental model is an addition-crosslinking silicone.

The addition-crosslinking silicones are cold-crosslinking two-component systems in which two pastes are mixed and cure with one another at room temperature after a few minutes. The substance class features extremely low shrinkage during crosslinking and generally reproduces the situation of which an impression is to be made with the correct dimensions and detail. The base paste contains polysiloxanes comprising polyatomic crosslinkable groups, organohydropolysiloxanes, filler and additives. The catalyst paste comprises a second proportion of the polysiloxanes comprising polyatomic crosslinkable groups, the catalyst for the crosslinking, likewise filler, and further additives.

The curing here is a catalyzed addition reaction which proceeds through hydrosilylation, a reaction of organohydropolysiloxanes (polysiloxanes having firstly organic groups and secondly Si—H bonds) onto polysiloxanes comprising polyatomic crosslinkable groups, generally unsaturated crosslinkable groups and preferably (optionally substituted) alkenyl groups, especially vinyl or allyl groups.

If the polymerizable material for production of a dental model is formed by an addition-crosslinking silicone, the following should be noted with regard to selection of constituents A.a.1-A.a.5.

A.a

In the polysiloxanes comprising polyatomic crosslinkable groups, it is preferable that one or more of the siloxanes comprising optionally substituted alkenyl groups is/are linear (i.e. unbranched in the siloxane base skeleton). In such a linear siloxane, two of the (optionally substituted) alkenyl groups, especially vinyl or allyl groups, per molecule are arranged at the chain ends (terminally).

Optionally, additional groups of this kind are present within the chain (i.e. non-terminally) to increase the degree of crosslinking, but preferably not too high a number, for instance one or two per molecule or no additional groups of this kind at all within the chain, since they cause the material to lose its elastic properties and become stiffer and more brittle.

Likewise optional is the use of branched siloxanes comprising optionally substituted alkenyl groups.

Likewise optional is the use of what are called VQM siloxanes (vinyl-terminated quaternary modified siloxanes) in addition to linear siloxanes. It is advantageous when these consist of molecules each having one silicon atom substituted by four siloxane chains, at the end of each of which is a vinyl group.

Such siloxanes lead to a gain in hardness of the crosslinked material without having to accept any great loss of flexibility or any great brittleness, and may thus constitute an alternative to fillers which in some cases increase the brittleness.

Very particular preference is given to the use of linear vinylmethylpolysiloxanes. These have terminal dimethylvinylsiloxane units. Very particular preference is additionally given to the use of several different polysiloxanes, especially of linear vinylmethylpolysiloxanes having different viscosities. For instance, very particular preference is given to a mixture of two linear vinylmethylpolysiloxanes; for example, a linear vinylmethylpolysiloxane comprising terminal vinyl groups has a viscosity in the range from 200 mPas up to and including 2500 mPas, and a further linear vinylmethylpolysiloxane comprising terminal vinyl groups a viscosity in the range from greater than 2500 mPas to 65 000 mPas. The viscosity figures for the constituents are based on the dynamic viscosities which are determined to DIN 53018 at 25° C.

The amount of the linear vinylmethylpolysiloxanes based on the total amount of the polymerizable material for production of a dental model is 10-40% by weight, preferably 15-35% by weight and more preferably 20-30% by weight, where the weight ratio of the low-viscosity to higher-viscosity siloxane is the range from 6:1 to 1:4, preferably 5:1 to 1:4 and more preferably 3:1 to 1:2.5.

A.a.2

The organohydropolysiloxanes are alkylhydropolysiloxanes (polysiloxanes having firstly alkyl groups and secondly Si—H bonds), where the alkyl groups preferably each bear 1 to 4 carbon atoms and are more preferably methyl groups. Organohydropolysiloxanes having at least 3 Si—H bonds per molecule are used as crosslinkers. In addition, it is also possible to use organohydropolysiloxanes having 2 Si—H bonds per molecule as what are called chain extenders for influencing the curing characteristics and the elasticity characteristics.

Alternatively to the use of the VQM siloxanes, a gain in hardness can also be gained on the part of the alkylhydropolysiloxanes without any great loss of flexibility of the polymer. For example, linear α,ω-divinyl-terminated polydimethylsiloxanes can be crosslinked using tetrakis(dimethylsiloxy)silane as a tetrafunctional crosslinker. Unlike the alkylhydropolysiloxanes typically used, which are in the form of oligomeric mixtures, this crosslinker is a defined molecule.

Preferably, the organohydropolysiloxanes have two to three Si—H bonds per molecule. Preference is given here to terminal bonds, but they may also additionally or exclusively be within the chain. Organo-hydropolysiloxanes whose Si—H bonds are within the chain are preferably comparatively short.

Very particular preference is given to the use of organohydropolysiloxanes having three Si—H bonds per molecule.

The amount of organohydropolysiloxanes is calculated stoichiometrically relative to the amount of polysiloxanes comprising polyatomic crosslinkable groups. It is generally 2-10% by weight, preferably 3-9% by weight and more preferably 4-8% by weight, based on the total composition of the polymerizable material for production of a dental model.

A.a.3

The catalysis for the reaction of a polydimethylsiloxane comprising polyatomic crosslinkable groups, preferably unsaturated crosslinkable groups, with a polydimethylsiloxane comprising Si—H functionalities proceeds with involvement of metal complexes, where the Si—H group can add both onto C—C double bonds and C—C triple bonds, and onto heteroatom multiple bonds. Suitable catalysts are Pt, Pd, Rh, Ni, Os or Co. In a preferred form, the metals are used in complexed form in amounts of 0.1 to 1% by weight based on the total mass of the addition-crosslinking silicone. The catalyst used is more preferably platinum as a Pt(0) complex with vinylsiloxane ligands. By way of example, the Karstedt catalyst is mentioned as a particularly preferred catalyst, this being formed in the reaction of divinyltetramethyldisiloxane with hexachloroplatinic acid by reduction and complexation of the platinum. The Karstedt catalyst is a Pt(0) complex having both bridge-forming and chelating divinyl ligands.

Other suitable and preferentially used platinum-siloxane complexes which accelerate the addition crosslinking are described, for example in documents U.S. Pat. No. 3,715,334 A, U.S. Pat. No. 3,775,352 A and U.S. Pat. No. 3,814,730 A.

The platinum catalyst is used in amounts in the range from 0.0002 to 0.04% by weight, preferably in the range from 10 to 100 ppm by weight and more preferably in the range from 15 to 50 ppm by weight, in each case calculated as elemental platinum, based on the total weight of all constituents of the polymerizable material for production of a dental model.

In some cases, it is appropriate to use a plurality of catalysts.

A.a.4

The polymerizable material for production of a dental model further comprises fillers, since unfilled silicones after curing are often still too elastic and still have unsuitable properties for use as a modeling material. The fillers are used in order to establish and to optimize the desired physical prerequisites. Even a (very) highly adjusted crosslinking density of the silicone elastomer is unable to make up for the action of a filler.

The preferred fillers are, for example, cristobalite, silicates, montmorillonites, bentonites, metal oxide powders such as aluminum oxides or zinc oxides and mixed oxides thereof, titanium dioxide, magnesium oxide, gypsum, inorganic salts such as sulfates, carbonates and glass. Preference is additionally given to crystalline silica, such as pulverized quartz or diatomaceous earth, and amorphous silica in the form of fumed silicas. The preferred fillers also include nanoscale silicas which are in the form of non-aggregated and non-agglomerated particles and are producible, for example, by the sol-gel method.

The fillers may be surface-treated and preferably hydrophobized in the process, for example by the treatment of their surfaces with organosilanes.

The fillers are selected so as to result in a Shore D hardness, determined to DIN 53505, of the crosslinked impression of 25 to 85, preferably in the range from 30 to 80.

The filler may be accommodated in one and/or another component of the two-component material. It is preferably added to both components in similar amounts.

In general, the fillers are used in amounts of more than 50-90% by weight, preferably of 52-80% by weight and more preferably of 55-65% by weight, based on the total weight of the polymerizable material for production of a dental model.

A.a.5

A particularly preferred configuration of the polymerizable material for production of a dental model has additional constituents according to feature A.a.5.

The reaction between the two components takes place at ambient temperature and is complete within a few minutes. It is therefore necessary in many cases to use a reaction retardant, also called an inhibitor, in order to control the reaction. In general, the retardant component comprises any unsaturated substances which have low molecular weight and are consumed in the polymerization at the start, in order to delay curing. Such inhibitors are described, for example, in publications U.S. Pat. No. 3,933,880 A, U.S. Pat. No. 3,445,420 A and U.S. Pat. No. 3,989,667 A. Examples thereof are acetylenically unsaturated alcohols such as 3-methyl-1-butyn-3-ol, 1-ethynylcyclohexan-1-ol or 3-methyl-1-pentyn-1-ol. They can be used individually or together. It is also possible to utilize vinylsiloxane-based compounds such as 1,1,3,3-tetramethyl-1,3-divinyldisiloxane and/or vinyl-containing oligo- and disiloxanes.

The amount of the inhibitor component used with preference is determined primarily by the type of inhibitor used, and so no general ranges can be specified. If, for example, 1,3-divinyltetramethyldisiloxane is used, at least 0.05 to 0.15% by weight, based on the overall composition, has to be used. If an ethynylically unsaturated alcohol is employed, 0.001-0.10% by weight, preferably 0.002-0.05% by weight and more preferably 0.005-0.01% by weight is sufficient, based on the total weight of the polymerizable material for production of a dental model.

Inhibitors used with particular preference are therefore ethynylically unsaturated alcohols.

In the course of crosslinking of the polysiloxane system, hydrogen may be released. For this reason, a metal is added, preferably in finely distributed form, to the polymerizable material for production of a dental model. The metal used is preferably platinum or palladium. The metal may also be deposited on a salt. The platinum is used in an amount of 1 to 1000 ppm, preferably 1 to 500 ppm and more preferably 10 to 50 ppm.

Stabilizers added to the polymerizable material for production of a dental model are likewise water-absorbing inorganic solids such as anhydrous calcium sulfate, calcium chloride or similar compounds, or water-adsorbing compounds such as zeolites, molecular sieves or similar substances. The amount of the water-adsorbing substance is between 0.1 and 5% by weight, preferably between 0.25-4% by weight and more preferably between 0.5-2% by weight. The stabilizers can be used individually or in a plurality.

Through the controlled use of polymer powders and/or ultrahigh molecular weight siloxanes as rheology modifiers, it is possible to control the rheological properties of the polymerizable material for production of a dental model such that machine mixing and dischargeability of the material during use is facilitated. It has been found that materials without the non-reinforcing additives mentioned below have good machine dischargeability, but the use of these enables a discharge rate higher than usual. The amount of the rheology modifiers is in the range between 1 and 10% by weight. The rheology modifiers, even though they are solid materials, are not counted with feature A.a.4.

The rheology modifiers also include solids composed of silicone resins which are soluble in the silicone polymer. The rheology modifiers can be added individually or in a plurality.

In addition, the composition may optionally comprise dyes such as pigments, and wetting agents (surface-active agents) such as surfactants and antioxidants.

The base paste and catalyst paste are present in a volume ratio in a range from 10:1 to 1:10.

The person skilled in the art is capable of selecting the catalyzing and retarding components A.a.3 and A.a.5 so as to result in suitable processing and setting times.

If the polymerizable material for production of a dental model is formed by an addition-crosslinking silicone, the low deformation under pressure with simultaneously adequately low viscosity is formed through an appropriately high filler content and a mixture of functionalized polydimethylsiloxanes of different viscosity.

A.b

Polyether materials are copolymers formed from alkylene oxide and tetrahydrofuran. The base paste generally contains relatively long-chain linear copolymers formed from ethylene oxide and butylene oxide units. The terminal OH groups are esterified with unsaturated acids and then react with ethyleneimine. This gives rise to reactive aziridine groups at the chain end. Ethyleneimine, as a three-membered heterocyclic ring, is very reactive and can be cleaved easily.

Polyethers are described, for example, in DE 197 53 456 B4 or DE 100 01 747 C2. These are two-component, cationically curing preparations. These involve curing of N-alkylaziridine compounds under the action of acidic compounds in the manner of a cationic polymerization. The catalytic presence of a cationic initiator results in polyaddition, and the components react to give the crosslinked end product.

Polyethers as described, for example, in WO 01/92374 A1 consist of N-alkylaziridino block copolymers, starter substances suitable for bringing about the curing of the N-alkylaziridino block copolymers, organic diluents and modifiers. These modifiers are usually finely divided solids such as aluminosilicates, precipitated silicas, quartz flour, wollastonite, mica flour and diatomaceous earth, and also dyes and pigments, the addition of which enables better assessment of the mixing quality and reduces the risk of confusion, thixotropic agents such as finely dispersed silicas, and other additions which influence the flow characteristics, such as polymeric thickeners, and also surface-active substances for adjusting the inflow characteristics, and odorants and flavorings.

DE 102 35 990 A1 describes polyethers which have improved demoldability and improved inflow characteristics, and comprise, for example, aziridino-bearing compounds, compounds which bring about softening of the cured dental materials, fillers, and further active ingredients such as colorants, aromas, initiators, crosslinkers, accelerators, rheological additives, bodying agents and surfactants.

DE 603 00 415 12 also describes polyether materials consisting of N-alkylaziridine polyethers, components containing $SO_2NH$ groups, including arylsulfonamides and/or alkylsulfonamides, activators which can initiate the curing operation, and optionally additives such as modifiers, fillers, dyes, pigments, thixotropic agents, flow improvers, polymer thickeners, surface-active agents, fragrances, one or more diluents and flavorings. Fillers in this context are aluminosilicates, silicas, quartz powder, wollastonite, mica powder and diatomaceous earths.

An inventive kit for indirect production of composite inlays comprises, for example, a polymerizable material for production of a dental model based on polyethers, comprising 30-90% by weight of aziridine-bearing copolymers, 1-10% by weight of starter substances suitable for bringing about the curing of the aziridine-bearing copolymers, 3-45% by weight of fillers and 2-85% by weight of additives, where the percentages by weight are based on the total mass of the addition-crosslinking silicones.

Once a positive model of the cavity situation has been produced from the polymerizable material for production of a dental model, in the next step of the way described here of producing a composite inlay using the inventive kit, the restoration which is to be bonded later in the cavity is modeled and polymerized in the model of the cavity with a polymerizable material for production of an inlay. The polymerizable material for production of an inlay is therefore selected from the polymerizable materials typically used for production of tooth restorations.

These also include the carbosilane systems described, for example, in publications EP 1 773 281 B1, EP 1 765 265 B1, EP 1 765 264 A1, EP 1 765 263 A1 and 1 765 261 A1, and additionally also the ormocer systems disclosed, for example, in patent specifications EP 1 685 182 B1, EP 1 871 333 B1, EP 1 874 847 B1, DE 41 33 494 C2, EP 0 450 624 B1, EP 0 682 033 B1, EP 1 377 628 B1, EP 2 004 131 B1, DE 195 08 586 C2, DE 103 39 912 A1, US 2011/0110998 A1 and EP 1 159 281 B1, and additionally also the monomers which cure via ring-opening metathesis polymerization and are proposed, for example, in documents DE 199 05 093 A1, DE 197 42 980 A1 and US 2010/0036015 A1.

Preference is given, however, to the conventional light-curing filling materials based on standard (meth)acrylate-functionalized monomers, as adequately described in the prior art. The above-described ormocer systems, like the "dental standard monomers", crosslink by free-radical means via (meth)acrylate functions, and so the ormocers in the context of this invention are always counted among the "standard dental monomers".

If the polymerizable material for production of an inlay is formed by methacrylate-based composite materials, the following should be noted with regard to the selection of constituents B.a.1-B.d.

B.a.1-B.d

The polymerizable material for production of an inlay contains a proportion of filler particles of more than 75% by weight (i.e. >75% by weight), preferably 80% by weight to 95% by weight, based on the total mass of the polymerizable material for production of an inlay. The filler component comprises a mixture of a first filler (B.a.1) in the form of organically surface-modified nanoparticles having a mean primary particle size <(less than) 200 nm and a second filler (B.a.2) in the form of microparticles having a mean particle size in the range from 0.4 μm to 10 μm. The combination of nanoparticles (B.a.1) and microparticles (B.a.2) in the polymerizable material for production of an inlay achieves complete and homogeneous volume filling of the composite material. This firstly reduces the shrinkage of the composite material in the course of curing of the polymer matrix, and secondly increases the mechanical strength, specifically the flexural strength.

The median particle size $d_{50}$ of the filler particles to be used in the filler component B.a.2 of the composite material to be used as the polymerizable material for production of an inlay is determined by means of light scattering (laser diffraction), preferably with a Beckman Coulter LS 13320 particle measuring instrument.

Component B.a.1: Organically Surface-Modified Nanoparticles

Within the polymerizable material for production of an inlay, one of the functions of the nanoparticles is to occupy the interstices between the microparticles in order thus to bring about homogeneous filling of the polymerizable material for production of an inlay, and to increase the strength, hardness and abrasion resistance. Nanoparticles in the context of the present invention are understood to mean particles having a mean primary particle size of less than 200 nm. The mean primary particle size is preferably less than 100 nm and more preferably less than 60 nm. The smaller the nanoparticles are, the better they can fulfill their function of filling the cavities between the microparticles.

The proportion of organically surface-modified nanoparticles having a mean primary particle size less than 200 nm is at least 2% by weight, preferably at least 8% by weight and more preferably at least 12% by weight. In in-house studies, it has been found that, in the case of a content of 8% by weight or less of organically surface-modified nanoparticles having a mean primary particle size less than 200 nm, the composite material in individual cases no longer has sufficient abrasion resistance. One reason for this is probably that, in the case of a content of 2% by weight or less of said nanoparticles, the cavities between the microparticles having a mean particle size of 0.4 μm to 10 μm are no longer sufficiently filled. On the other hand, it has been found that, in the case of a content of more than 30% by weight of organically surface-modified nanoparticles having a mean primary particle size less than 200 nm, the processability of the composite material is no longer adequate; because of the high solids content, the viscosity thereof then becomes too high.

The materials for the nanoparticles to be used are preferably oxides or mixed oxides and are preferably selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof. The preferred oxidic nanoparticles are not agglomerated.

In a very preferred configuration, the nanoscale particles are in non-agglomerated and non-aggregated form, for example dispersed in a medium, preferably in monodisperse form.

In order to enable good binding of the nanoparticles into the polymer matrix of a polymerizable material for production of an inlay of an inventive kit, the surfaces of the nanoparticles (preferably of the preferred oxidic nanoparticles) have been organically modified, i.e. their surfaces have organic structural elements. Examples include the surface treatment of the fillers with a silane. A particularly suitable adhesion promoter is γ-methacryloyloxypropyltrimethoxysilane.

Component B.a.2: Microparticles having a mean particle size in the range from 0.4 μm to 10 μm Within the polymerizable material for production of an inlay, the microparticles bring about substantially homogeneous filling of the volume, with at least partial filling of the remaining cavities between the microparticles by the above-described nanoparticles (component B.a.1). Microparticles in the context of the present invention are understood to mean particles having a mean particle size of 400 nm to 10 μm. The mean particle size is preferably smaller than 5 μm. In in-house studies, it has been found that the smaller the microparticles, the more complete and homogeneous is the volume filling of the composite material achievable with the microparticles alone. The total amount of component B.a.2 is in the range from 45 to <(less than) 85% by weight, preferably 65 to 85% by weight, of microparticles based on the total mass of the polymerizable material for production of a composite inlay B.

The microparticles of component B.a.2 may have a monomodal or multimodal, for example a bimodal, particle size distribution. Microparticles having a bimodal or multimodal particle size distribution are preferred, since more complete volume filling is achievable therewith than in the case of general use of microparticles with monomodal particle size distribution. In the case of presence of a bi- or multimodal particle size distribution, the particles of the fractions with the greater particle size bring about coarse filling of the volume, while the particles of the fraction with the smaller particle size, as far as possible, fill the cavities between the particles of the fractions with the greater particle size. The cavities still remaining are filled by nanoparticles as described above.

Preference is thus given to using, in a polymerizable material for production of an inlay, a component B.a.2 comprising two or more fractions of microparticles with different mean particle sizes of the fractions.

The microparticles of different fractions may consist of the same material or of different materials; it is possible for several fractions of microparticles to be present, the mean particle size of which is virtually the same or is within a particular range, in which case the materials of the particles differ between the fractions.

The base materials for the microparticles to be used in surface-modified form are preferably selected from the group consisting of amorphous materials based on $SiO_2$, $ZrO_2$ and/or $TiO_2$, and also mixed oxides, fumed silicas or precipitated silicas, such as quartz glass ceramics or glass powders (especially dental glass powders), barium glasses or strontium glasses, fluoride ion-releasing glasses, oxides of aluminum or silicon, zeolites, apatites, zirconium silicates, sparingly soluble metal salts such as barium sulfate or calcium fluoride, and X-ray-opaque fillers such as ytterbium fluoride.

For better binding into the polymer matrix of a polymerizable material for production of an inlay of an inventive kit, the microparticles have preferably been organically surface-modified. Mention should be made by way of example of the surface treatment of the fillers with a silane, which leads to silanized microparticles. For surface treatment (as an adhesion promoter), γ-methacryloyloxypropyltrimethoxysilane is particularly suitable.

In a particularly preferred polymerizable material for production of an inlay, at least a portion of the microparticles of component B.a.2 is formed by organically surface-modified particles, preferably silanized particles, and/or at least a portion of the microparticles of component B.a.2 is formed by dental glass particles; preferably, at least a portion of the microparticles of component B.a.2 are organically surface-modified dental glass particles, preferably silanized dental glass particles.

Preferably, in these cases, component B.a.2 is notable for a bi- or multimodal particle size distribution, especially a bi- or multimodal particle size distribution.

Component B.a.3: Further Fillers

As well as components B.a.1 and B.a.2, the mixture of filler particles may additionally comprise further fillers as component B.a.3.

For example, it is possible to use reinforcing filler materials such as glass fibers, or polyamide or carbon fibers. The polymerizable material for production of an inlay of an inventive kit may also comprise fine chips or bead polymers, where the bead polymers may be homo- or copolymers of organically curable monomers.

Constituent B.b: Monomer Mixture

Within a polymerizable material for production of an inlay of an inventive kit, the function of the monomer mixture B.b is to form a matrix into which the abovementioned fillers B.a are incorporated. This matrix is formed by curing, or crosslinking, of suitable monomer units, such as the conventional dental (meth)acrylate monomers listed below, and also carbosilanes and monomers which cure via ring-opening metathesis polymerization.

This matrix is preferably formed by respective free-radical polymerization of B.b.1 one, two or more monomers selected from the group comprising 2,2-bis[4-(2-hydroxy-3-(meth)acryloyloxypropoxy)phenyl]propane (bis-GMA), bisphenol A glycidyl di(meth)acrylate, bisphenol B glycidyl di(meth)acrylate, bisphenol C glycidyl di(meth)acrylate, bisphenol F glycidyl di(meth)acrylate, alkoxylated bisphenol A glycidyl di(meth)acrylate (e.g. ethoxylated bisphenol A glycidyl di(meth)acrylate, propoxylated bisphenol A glycidyl di(meth)acrylate, ethoxylated bisphenol A dimethacrylate, 7,7,9-trimethyl-4,13-dioxo-5,12-diazahexadecane 1,16-dioxydimethacrylate (UDMA), ormocers, and TCD (tricyclodecane derivatives) free-radically polymerizable via (meth)acrylate groups, such as TCD-di-HEMA (bis(methacryloyloxymethyl)tricyclo[5.2.1.0$^{2,6}$]-decane) and/or TCD-di-HEA (bis(acryloyloxymethyl)-tricyclo[5.2.1.0$^{2,6}$] decane), and polymerizable compounds comprising a polyalicyclic structural element, as known from EP 2 436 668 B1, which form part of the present application by way of reference.

Component B.b.2: One, Two or More Further Free-Radically Polymerizable Monomers from the Group Consisting of Acrylates and Methacrylates, Preferably from the Group of the Methacrylates The second constituent of the matrix-forming monomer mixture which does not form part of component B.b.1 is formed by free-radically polymerizable monomers selected from the group consisting of acrylates and methacrylates. Their function within the polymerizable material for production of an inlay consists essentially in the establishment of the viscosity.

Because of their higher biocompatibility, the methacrylic esters or diesters are preferred over the corresponding acrylic esters or diesters.

The patent literature mentions a multitude of diacrylate and dimethacrylate monomers (for example including DE 39 41 629 A1, which is part of the present application by way of reference, especially the disclosure in the section from column 6 line 15 to column 8 line 10), which are suitable for use in a polymerizable material for production of an inlay.

A preferred polymerizable material for production of an inlay comprises, in component B.b.2, one or more di(meth) acrylate monomers selected from the group consisting of ethylene glycol (dimeth)acrylate (EGDMA), 1,6-hexanediol (dimeth)acrylate (HEDMA), triethylene glycol (dimeth) acrylate (TEDMA), 1,12-dodecanediol (dimeth)acrylate (DODMA), decanediol (dimeth)acrylate, polyethylene glycol (dimeth)acrylate (PEGDMA), butanediol di(meth)acrylate, tetraethylene glycol (dimeth)acrylate, neopentyl glycol (dimeth)acrylate, 2-hydroxypropyl 1,3-di(meth)acrylate, 3-hydroxypropyl 1,2-(dimeth)acrylate, pentaerythritol (di-meth)acrylate and glyceryl(dimeth)acrylate.

The free-radically polymerizable monomers of component B.b.2, which thus do not form part of component B.b.1, may also be hydroxyl compounds. In this context, it is possible to use all hydroxyl compounds of acrylates or methacrylates customarily used in dental chemistry. Preference is given to hydroxyl compounds of (meth)acrylates, of which preference is given in turn to 2-hydroxyethyl(meth) acrylate, 2-hydroxypropyl(meth)acrylate, 3-hydroxypropyl (meth)acrylate, 1,2-dihydroxypropyl(meth)acrylate, 1,3-dihydroxypropyl(meth)acrylate, 2,3-dihydroxypropyl(meth) acrylate, 2-hydroxypropyl 1,3-di(meth)acrylate and 3-hydroxypropyl 1,2-di(meth)acrylate.

A polymerizable material for production of an inlay may further comprise, in component B.b.2, one or more acrylate and/or methacrylate monomers containing acid groups. Such monomers containing acid groups may preferably have a carboxylic acid, phosphoric acid, phosphonic acid, sulfonic acid and/or thiophosphoric acid function. The monomer may contain one acid function or a multitude of acid functions in one molecule.

Suitable monomers containing a phosphoric acid group are, for example, 2-(meth)acryloyloxyethyl dihydrogenphosphate, bis[2-(meth)acryloyloxyethyl]hydrogenphosphate, 2-(meth)acryloyloxyethyl phenyl hydrogenphosphate, 6-(meth)acryloyloxyhexyl dihydrogenphosphate, 10-(meth)acryloyloxydecyl dihydrogenphosphate (MDP), 1,3-di(meth)acryloyloxypropane 2-dihydrogenphosphate, 1,3-di (meth)acryloyloxypropane 2-phenyl hydrogenphosphate and bis[5-(2-(meth)acryloyloxyethoxycarbonyl)heptyl]hydrogenphosphate.

Suitable monomers containing a carboxylic acid group are, for example, 4-(meth)acryloyloxyethyltrimellitic acid (4-MET), 4-(meth)acryloyloxyethyltrimellitic anhydride (4-META), 4-(meth)acryloyloxydecyltrimellitic acid, 4-(meth)acryloyloxydecyltrimellitic anhydride, 11-(meth) acryloyloxy-1,1-undecanedicarboxylic acid, 1,4-di(meth) acryloyloxypyromellitic acid, 2-(meth)acryloyloxyethylmaleic acid, 2-(meth)acryloyloxyethylphthalic acid and 2-(meth)acryloyloxyethylhexahydrophthalic acid.

Further suitable monomers bearing acid groups are mentioned, for example, in EP 0 980 682 A1 (especially paragraphs [0059] to [0065]) or EP 0 948 955 A1 (especially paragraphs [0031] to [0034]), and especially polymerizable phosphoric acid derivatives bearing a polyalicyclic structural element, as proposed in EP 2 450 025 A1, which likewise form part of the present application by way of reference.

In addition, it is also possible to use the phosphoric esters with glyceryl dimethacrylate or with hydroxyethyl methacrylate or with hydroxypropyl methacrylate.

The monomers mentioned may be used individually or in mixtures.

The ratio here of the mass of components B.b.1 to the mass of components B.b.2 is in the range from 1:10 to 10:1.

Constituent B.c and/or D.d: Initiators and/or Catalysts

The polymerizable materials B, C and D are preferably light-curable and/or chemically curable and contain, as constituent B.c and/or C.c and/or D.d, initiators and/or catalysts.

Preferred polymerizable materials for production of an inlay are light-curable (photocurable) and comprise light-curing initiators. Examples of a light-curing initiator include substances which have merely photosensitizing action, and combinations of sensitizers and accelerators.

Preferred polymerizable materials C and D are both light-curing and chemically curing, and hence dual-curing.

Examples of photosensitizers are alpha-diketones, benzoin alkyl ethers, thioxanthones, benzophenones, acylphosphine oxides, acetophenones, ketals, titanocenes, sensitizing dyes, etc. The sensitizers may be employed alone or in combination. Specific substance examples of the different classes can be found, for example, in DE 10 2006 019 092 A1 or in DE 39 41 629 C2, which form part of the present application by way of reference.

Examples of accelerators which are used together with the sensitizers are tertiary amines, secondary amines, barbituric acids, tin compounds, aldehydes and sulfur compounds. Specific substance examples of the different classes can be found in DE 10 2006 019 092 or in DE 39 41 629 C2, which form part of the present application by way of reference.

Further suitable initiators and initiator combinations are described in DE 601 16 142, which form part of the present application by way of reference.

The photoinitiators usable in the context of the present invention are characterized in that they can bring about the curing of a polymerizable material for production of an inlay through absorption of light in the wavelength range from 300 nm to 700 nm, preferably from 350 nm to 600 nm and more preferably from 380 nm to 500 nm, optionally in combination with one or more coinitiators.

The absorption maximum of camphorquinone (CC) is at about 470 nm and is thus within the blue light range. Camphorquinone (CC) is one of the $PI_2$ initiators and is regularly used together with a coinitiator.

Preferably, a polymerizable material for production of an inlay comprises the combination of an alpha-diketone and an aromatic tertiary amine, preference being given to the combination of camphorquinone (CC) and ethyl p-N,N-dimethylaminobenzoate (DABE).

Likewise preferable is the further combination of the "alpha-diketone/aromatic tertiary amine" system with a phosphine oxide, especially with phenylbis(2,4,6-trimethylbenzoyl)phosphine oxide and/or 2,4,6-trimethylbenzoyldiphenylphosphine oxide. With regard to the structures of suitable phosphine oxides for use in a polymerizable material for production of an inlay, reference is made to publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which form part of the present application by way of reference.

The phosphine oxides specified in these publications are particularly suitable alone or in combination with the "alpha-diketone/amine" system as a photopolymerization initiator system in a polymerizable material for production of an inlay.

Alternatively, borate salts, as described, for example, in U.S. Pat. No. 4,772,530, U.S. Pat. No. 4,954,414, U.S. Pat. No. 4,874,450, U.S. Pat. No. 5,055,372 and U.S. Pat. No. 5,057,393, may also find use as photoinitiators, these forming part of the present application by way of reference.

Further suitable photoinitiators are described in J.-P. Fouassier, Photoinitiation, Photopolymerization and Photocuring, Hanser Publishers, Munich, Vienna, New York 1995 and in J. F. Rabek (Ed.), Radiation Curing in Polymer Science and Technology, Vol. II, Elsevier Applied Science, London, New York 1993, which form part of the present application by way of reference.

The person skilled in the art is aware of various initiators for chemical curing. In this regard, reference is made by way of example to EP 1 720 506.

Preferred initiators for chemical curing are benzoyl peroxide, lauroyl peroxide, especially dibenzoyl peroxide, in combination with amines such as N,N-dimethyl-p-toluidine, N,N-dihydroxyethyl-p-toluidine, and structurally related amines.

The peroxides and the amines are divided between two different components of the dental material. When the amine-containing component (called the base paste) is mixed with the peroxide-containing component (called the initiator or catalyst paste), the reaction of amine and peroxide (redox reaction) initiates the free-radical reaction.

Dual-curing systems comprise a combination of photoinitiators and initiators for chemical curing.

For example, the base paste may additionally comprise a photoinitiator, such that the base paste can be used either solely as a light-curing dental material or, together with the initiator paste, as a light- and self-curing dental material.

As well as the oxidatively active organic peroxide compounds, the redox systems used may also be barbituric acids or barbituric acid derivatives and malonylsulfamides.

Among the barbituric acid systems, the "Bredereck systems" are of high significance. Examples of suitable "Bredereck systems" and references to the corresponding patent literature can be found in EP 1 839 640 B1 and in DE 1 495 520 B, WO 02/092021 A1 or in WO 02/092023 A1, which form part of the present application by way of reference.

Suitable malonylsulfamides are described in EP 0 059 451 B1, which forms part of the present application by way of reference. Preferred compounds in this context are 2,6-dimethyl-4-isobutylmalonyl-sulfamide, 2,6-diisobutyl-4-propylmalonylsulfamide, 2,6-dibutyl-4-propylmalonylsulfamide, 2,6-dimethyl-4-ethylmalonylsulfamide and 2,6-dioctyl-4-isobutyl-malonylsulfamide.

In addition, it is possible to use sulfur compounds in the +2 or +4 oxidation state, such as sodium benzenesulfinate or sodium para-toluenesulfinate.

As well as the conventional "Bredereck systems", it is also possible to use salts of barbituric acids or of barbituric acid derivatives or salts of thiobarbituric acids or of thiobarbituric acid derivatives, as described, for example, in EP 2 239 275 B1, EP 2 034 946 B1, JP 2006-299202, DE 10 2007 050 763 A1, U.S. Pat. No. 6,288,138 B1, DE 11 2006 001 049 T5, EP 1 502 569 B1 and EP 2 070 935 A1.

In that case, one component of this two-component system contains the salt of the CH-acidic compound, while the other component comprises an acid of greater strength than the other (CH—)acidic compound. If the two components are mixed, the CH-acidic compound is released by the stronger acid and can initiate the crosslinking.

To accelerate the curing, the polymerization can be performed in the presence of heavy metal compounds such as Ce, Fe, Cu, Mn, Co, Sn or Zn, particular preference being given to copper compounds. The heavy metal compounds are preferably used in the form of soluble organic compounds. Preferred copper compounds here are copper benzoate, copper acetate, copper ethylhexanoate, copper di(methacrylate), copper acetylacetonate and copper naphthenate.

Constituent B.d: Optional Further Additives

The polymerizable material for production of an inlay comprises, in some cases, one or more further additives.

These additives may have various functions. Standard additives for use in dental composite materials are known to those skilled in the art; he will select the suitable additive(s) according to the desired function. Examples of typical additives and functions thereof are described hereinafter.

Light-curable polymerizable materials for production of an inlay, as are preferred, preferably comprise one or more inhibitors, also called stabilizers. These are typically added in order to avoid spontaneous polymerization. They react with prematurely formed free radicals, which are scavenged, prevent premature polymerization and increase the storage stability of the light-curable dental composition. Standard inhibitors are phenol derivatives such as hydroquinone monomethyl ether (HQME) or 2,6-di-tert-butyl-4-methylphenol (BHT). Further inhibitors such as and tert-butylhydroxyanisole (BHA), 2,2-diphenyl-1-picrylhydrazyl radicals, galvinoxyl radicals, trimethylphenyl radicals, 2,3,6,6-tetramethyl-piperidinyl-1-oxyl radicals (TEMPO) and derivatives of TEMPO or phenothiazine and derivatives of this compound are described in EP 0 783 880 B1, which forms part of the present application by way of reference. Alternative inhibitors are specified in DE 101 19 831 A1 or in EP 1 563 821 A1, which form part of the present application by way of reference.

A polymerizable material for production of an inlay thus comprises, as an additive, one or more polymerization inhibitors for increasing the storage stability of the polymerizable material, preferably selected from the group consisting of hydroquinone monomethyl ether (HQME), phenols, preferably 2,6-di-tert-butyl-4-methylphenol (BHT) and tert-butyl-hydroxyanisole (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof.

A polymerizable material for production of an inlay may comprise, as an additive, one or more fluoride-releasing substances, preferably sodium fluoride and/or amine fluorides.

UV absorbers capable of absorbing UV radiation, for example through their conjugated double bond systems and aromatic rings, are in some cases part of a polymerizable material for production of an inlay. Examples of UV absorbers are 2-hydroxy-4-methoxybenzophenone, phenyl salicylate, 3-(2'-hydroxy-5'-methylphenyl)benzotriazole or diethyl 2,5-dihydroxyterephthalate.

Since the teeth should be restored with maximum trueness to nature, it is necessary to provide the polymerizable material for production of an inlay of an inventive kit in a wide variety of different hues. For this purpose, generally inorganic dyes and organic pigments are utilized in very small amounts, which are thus regarded as an additive in preferred configurations.

Further optional additives are aromas.

C.a.1-C.f and D.a-D.g

Constituent C.d and/or D.a: Adhesion Monomers

In order to achieve adhesion to enamel and/or dentine, a polymerizable material for luting of an inlay or a polymerizable material for increasing the bond strength between luting cement and the hard substance of the tooth comprises one or more adhesion monomers.

Preference is given to polymerizable materials for luting of an inlay comprising one or more further adhesion monomers as component C.d.

As constituent C.d and/or D.a, a polymerizable material for luting of an inlay or a polymerizable material for increasing the bond strength between luting cement and the hard substance of the tooth comprises one or more adhesion monomers selected from the group consisting of polymerizable or nonpolymerizable acids or carboxylic anhydrides, preferably from the group consisting of phosphoric acids, phosphonic acids, carboxylic acids and salts thereof, carboxylic esters and carboxylic anhydrides, preferably in an amount in the range from 0.1 to 35% by weight, further preferably in an amount in the range from 0.25 to 25% by weight, especially preferably in an amount in the range from 0.5 to 15% by weight, based in each case on the total mass of the mixture.

Preferably, adhesion-promoting components C.d and/or D.a are selected from the group consisting of 2-(meth)acryloyloxyethyl dihydrogenphosphate, 6-(meth)acryloyloxyhexyl dihydrogenphosphate, 4-(meth)acryloyloxybutyl dihydrogenphosphate, 8-(meth)acryloyloxyoctyl dihydrogenphosphate, 2-(meth)acryloyloxynonyl dihydrogenphosphate, 11-(meth)acryloyloxyundecyl dihydrogenphosphate, 20-(meth)acryloyloxyeicosyl dihydrogenphosphate, 1,3-di(meth)acryloyloxypropyl 2-dihydrogenphosphate, 2-(meth)acryloyloxyethylphenyl dihydrogenphosphate, 10-(meth)acryloyloxydecyl dihydrogenphosphate (10-MDP), di(2-(meth)acyloyloxyethyl) pyrophosphate, di(2-(meth)acyloyloxypropyl) pyrophosphate, di(2-(meth)acyloyloxybutyl) pyrophosphate, di(2-(meth)acyloyloxypentyl) pyrophosphate di(2-(meth)acyloyloxyhexyl) pyrophosphate, di(2-(meth)acyloyloxydecyl) pyrophosphate, mono-, di- and/or triesters of phosphoric acid which are obtained by reaction of hydroxy-C2-C8-alkyl methacrylate (preferably hydroxyethyl methacrylate) or glyceryl dimethacrylate with phosphorus oxychloride, glyceryl dimethacrylate phosphate, pentaerythrityl trimethacrylate phosphate, dipentaerythrityl pentaacrylate phosphate, tetramethacryloyloxyethyl pyrophosphate, trimellitic acid 4-methacryloyloxyethyl ester (4-MET), trimellitic anhydride 4-methacryloyloxyethyl ester (4-META), pyromellitic acid dimethacrylate, pyromellitic acid glycerol dimethacrylate, methacryloyloxyethyl phthalate, methacryloyloxyethyl maleate, methacryloyloxyethyl succinate, 1,3-glycerol dimethacrylate maleate and dioxyethoxymethacrylic acid ethylenediaminetetraacetic ester (the latter described in EP 1 721 949 B1).

Further suitable adhesion-promoting compounds are polymerizable phosphoric acid derivatives bearing a polyalicyclic structural element, as described in EP 2 450 025 A1, which likewise form part of the present application by way of reference.

Adhesion monomers preferred in turn as components C.d and/or D.a of a polymerizable material for luting of an inlay or of a polymerizable material for increasing the bond strength between luting cement and the hard substance of the tooth are glyceryl dimethacrylate phosphate, pentaerythrityl trimethacrylate phosphate, dipentaerythrityl pentacrylate phosphate, tetramethacryloyloxyethyl pyrophosphate, trimellic acid 4-methacryloyloxyethyl ester (4-MET), trimellitic anhydride 4-methacryloyloxyethyl ester (4-META), pyromellitic acid dimethacrylate, pyromellitic acid glyceryl dimethacrylate, dioxyethoxymethacrylic acid ethylenediaminetetraacetic ester, and polymerizable phosphoric acid derivatives bearing a polyalicyclic structural element.

Adhesion-promoting compounds are also aldehydes, (such as glutaraldehyde), polymerizable alcohols (such as HEMA) and other suitable polar functional compounds.

Constituent C.b and/or D.b: Polymerizable Monomers

The polymerizable monomers are preferably free-radically light-polymerizable monomers which are substances having preferably one, two or more ethylenic groups, for example but not restricted to the (meth)acrylate monomers customarily used in dental chemistry.

The patent literature mentions a multitude of further compounds (for example including DE 39 41 629 A1, which forms part of the present application by way of reference), all of which are diesters of acrylic acid or methacrylic acid and are suitable for use in a polymerizable material for luting of an inlay or of a polymerizable material for increasing the bond strength between luting cement and the hard substance of the tooth in an inventive kit.

In a preferred polymerizable material, constituent C.b and/or D.d comprises one or more di(meth)acrylate monomers selected from the group consisting of ethylene glycol di(meth)acrylate, 1,6-hexanediol di(meth)-acrylate (HEDMA), triethylene glycol di(meth)acrylate (TEDMA), 1,12-dodecanediol di(meth)acrylate, ethoxylated bisphenol A di(meth)acrylate, polyethylene glycol dimethacrylate, 7,7,9-trimethyl-4,13-dioxo-5,12-diazahexadecane 1,16-dioxy-dimethacrylate (UDMA), butane diol dimethacrylate, tetraethylene glycol dimethacrylate, neopentyl glycol dimethacrylate, 2-hydroxypropyl 1,3-dimethacrylate, 3-hydroxypropyl 1,2-dimethacrylate, pentaerythrityl dimethacrylate, glyceryl dimethacrylate, bisphenol A glycidyl methacrylate (bis-GMA), ormocers, and TCD tricyclodecane derivatives free-radically polymerizable via (meth)acrylate groups, such as TCD-di-HEMA (bis(methacryloyloxymethyl)tricyclo[5.2.1.0$^{2,6}$]decane), TCD-di-HEA (bis(acryloyloxymethyl)tricyclo[5.2.1.0$^{2,6}$]-decane), and polymerizable compounds comprising a polyalicyclic structural element, as known from EP 2 436 668 B1, and which likewise form part of the present application by way of reference.

The free-radically light-polymerizable monomers may also be hydroxyl compounds having at least one ethylenic double bond. In this context, it is possible with preference to use the hydroxyl compounds of acrylates or methacrylates customarily used in dental chemistry. Preference is given to hydroxyl compounds of methacrylates, and preference is given in turn to 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythrityl dimethacrylate and glyceryl dimethacrylate.

A polymerizable material for luting of an inlay or a polymerizable material for increasing the bond strength between luting cement and the hard substance of the tooth is preferably characterized in that constituent C.b and/or D.b consists of or comprises one or more (meth)acrylate monomer(s), preferably selected from the group consisting of 2-hydroxyethyl(meth)acrylate (HEMA), bisphenol A glycidyl(meth)acrylate (bis-GMA), 7,7,9-trimethyl-4,13-dioxo-5,12-diazahexadecane 1,16-dioxydi(meth)acrylate (UDMA), triethylene glycol di(meth)acrylate (TEDMA), tetraethylene glycol di(meth)acrylate, polyethylene glycol di(meth)acrylate, trimethylolpropane tri(meth)acrylate (TMPTMA), dodecanediol di(meth)acrylate (DODMA), ormocers, and TCD (tricyclodecane) derivatives free-radically polymerizable via (meth)acrylate groups, such as TCD-di-HEMA (bis(methacryloyloxymethyl)tricyclo[5.2.1.0$^{2,6}$]-decane) and/or TCD-di-HEA (bis(acryloyloxymethyl)-tricyclo[5.2.1.0$^{2,6}$]decane), and polymerizable compounds comprising a polyalicyclic structural element, as known from EP 2 436 668 B1, glyceryl di(meth)acrylate, 1,6-hexanediol di(meth)acrylate (HEDMA), ethoxylated bisphenol A di(meth)acrylate, pentaerythrityl di(meth)acrylate, pentaerythrityl tri(meth)acrylate and dipentaerythrityl penta(meth)acrylate.

The total mass of the monomers of component C.b is in the range from 16.8 to less than 60% by weight, preferably in the range from 18 to 50% by weight, further preferably in the range from 20 to 40% by weight, based in each case on the total mass of a polymerizable material for luting of an inlay or of a polymerizable material for increasing the bond strength between luting cement and the hard substance of the tooth. The total mass of the monomers in component D.b is between 3 and 60% by weight. D.b optionally also contains solvent (including water) in the range of 0-80% by weight, and adhesion monomers in the range of 1-60% by weight.

Preferably, a polymerizable material for luting of an inlay or a polymerizable material for increasing the bond strength between luting cement and the hard substance of the tooth contains a mixture of two or more monomers of component C.b and/or D.b.

Preferred mixtures are characterized in that component C.b and/or D.b comprises one or more (meth)acrylate monomers selected from the group consisting of 2-hydroxyethylmethacrylate (HEMA), bisphenol A glycidyl methacrylate (bis-GMA), 7,7,9-trimethyl-4,13-dioxo-5,12-diazahexadecane 1,16-dioxydimethacrylate (UDMA), triethylene glycol dimethacrylate (TEDMA), tetraethylene glycol dimethacrylate, trimethylolpropane trimethacrylate (TMPTMA), glyceryl di(meth)acrylate, 1,6-hexanediol dimethacrylate (HEDMA), ethoxylated bisphenol A dimethacrylate and dipentaerythrityl penta(meth)acrylate, bis(methacryloyloxymethyl)tricyclo[5.2.1.0$^{2,6}$]decane) and/or (bis(acryloyloxymethyl)tricyclo[5.2.1.0$^{2,6}$]-decane) and mixtures thereof, and other TCD (tricyclodecane) derivatives free-radically polymerizable via (meth)acrylate groups and comprising a polyalicyclic structural element, as known from EP 2 436 668 B1, and which likewise form part of the present application by way of reference.

Constituent C.a and/or D.c: Fillers

As constituent C.a and/or D.c, it is possible to use organic and/or inorganic fillers.

If a polymerizable material for luting of an inlay comprises one or more fillers in component C.a, the total mass of the fillers is preferably in the range from 0.5 to 75% by weight, preferably in the range from 10 to 70% by weight, more preferably in the range from 30 to 65% by weight, based in each case on the total mass of a polymerizable material for luting of an inlay.

If a polymerizable material for increasing the bond strength between luting cement and the hard substance of the tooth comprises one or more fillers in component D.c, the total mass of the fillers is preferably in the range from 0 to 30% by weight, preferably in the range of 0 to 15% by weight, further preferably in the range of 0 to 8% by weight, based in each case on the total mass of a polymerizable material for increasing the bond strength between luting cement and the hard substance of the tooth.

Inorganic fillers can be used alone or as mixtures. For optimization of the product properties, the inorganic fillers can be introduced into the formulations in different particle sizes. The fillers may have a unimodal or multimodal, for example a bimodal, distribution.

The median particle size $d_{50}$ of the filler particles to be used in filler component C.a and/or D.c in a polymerizable material for luting of an inlay or a polymerizable material for increasing the bond strength between luting cement and the hard substance of the tooth is determined by means of light scattering (laser diffraction), preferably with a Beckman Coulter LS 13320 particle size measuring instrument.

The fillers of components C.a and D.c are selected depending on the end use of the respective polymerizable material.

For instance, the fillers in a polymerizable material for luting of an inlay are preferably used in the form of microparticles having a mean particle size in the range from 0.4 µm to 10 µm.

Microparticles in the context of the present invention are understood to mean particles having a mean particle size of 400 nm to 10 µm. The mean particle size is preferably less than 5 µm.

The microparticles of component C.a and/or D.c may have a monomodal or multimodal, for example a bimodal, particle size distribution. Microparticles having a bimodal or multimodal particle size distribution are preferred, since more complete volume filling is achievable therewith than in the case of general use of microparticles having monomodal particle size distribution. In the case of presence of a bi- or multimodal particle size distribution, the particles of the fractions having the greater particle size bring about coarse filling of the volume, while the particles of the fraction having the smaller particle size, as far as possible, will fill the cavities between the particles of the fractions having the greater particle size.

Preference is thus given, in a polymerizable material for luting of an inlay, to a component C.a comprising two or more fractions of microparticles, in which case the mean particle sizes of the fractions are different.

Preferably, component C.a comprises at least two microparticle fractions, in which case the mean particle sizes thereof differ from one another by at least 0.5 µm, preferably by at least 0.7 µm.

The microparticles of various fractions may consist of the same material or of different materials; it is also possible for several fractions of microparticles to be present, the mean particle size of which is approximately equal or is within a particular range, in which case the materials of the particles differ between the fractions.

For better incorporation into the polymer matrix of a polymerizable material for luting of an inlay or of a polymerizable material for increasing the bond strength between a luting cement and the hard substance of the tooth, the microparticles may be organically surface-modified. Examples include the surface treatment of the fillers with a silane, which leads to silanized microparticles. For surface treatment (as an adhesion promoter), γ-methacryloyloxypropyltrimethoxysilane is particularly suitable.

A polymerizable material comprising microparticles for luting of an inlay or a polymerizable material comprising microparticles for increasing the bond strength between luting cement and the hard substance of the tooth may additionally also comprise nanoscale fillers.

The inorganic fillers used may, for example, be compact glasses and different silicas in various sizes and states (monodisperse, polydisperse).

Suitable inorganic constituents are, for example, amorphous materials based on mixed oxides composed of $SiC_2$, $ZrO_2$ and/or $TiO_2$, microfine fillers such as fumed silica or precipitated silica, and macro- or minifillers such as quartz glass ceramic or glass powder, barium silicate glasses, barium fluorosilicate glasses, strontium silicate glasses, strontiumborosilicate, Li/Al silicate glasses, barium glasses, calcium silicates, sodium aluminum silicates, fluoroaluminum silicate glasses, oxides of aluminum or silicon, zeolites, apatite, zirconium silicates, sparingly soluble metal salts such as barium sulfate or calcium fluoride, and X-ray-opaque fillers such as ytterbium fluoride.

Preferred X-ray-opaque fillers are selected from the group consisting of zinc, ytterbium, yttrium, zirconium, strontium, calcium, titanium, tungsten, tantalum, niobium, barium, bismuth, molybdenum in the form of alloys, oxides, fluorides, oxo halides, sulfates, phosphates, silicates, carbonates, tungstates or glasses, and mixtures thereof.

Advantageous X-ray-opaque fillers are $CaWO_4$, $ZrO_2$, ytterbium fluoride, barium sulfate and/or X-ray-opaque glasses.

For adjustment of the rheology, the curable mixtures and products used in the inventive kit may comprise different silicas, preferably fumed silicas.

In addition, it is possible to use reinforcing materials such as glass fibers, polyamide fibers or carbon fibers. The curable mixtures and products may additionally comprise fine chips or bead polymers, in which case the bead polymers may be homo- or copolymers of organic curable monomers. The organic fillers can in principle be employed in different granularity, for example ground polymers and prepolymers.

Likewise preferably, a polymerizable material for luting of an inlay and/or a polymerizable material for increasing the bond strength between luting cement and the hard substance of the tooth comprises nanoscale solid particles. The nanoscale solid particles are particles having a mean particle size of not more than 200 nm, preferably not more than 100 nm and especially not more than 70 nm. The nanoscale inorganic solid particles are preferably those of oxides, phosphates, sulfides, selenides and tellurides of metals and mixtures thereof. Particular preference is given to nanoscale particles of $SiO_2$, $TiO_2$, $ZrO_2$, $ZnO$, $SnO_2$ and $Al_2O_3$, and mixtures thereof. The nanoscale solid particles are produced in a known manner, for example by flame pyrolysis, plasma processes, gas phase condensation, colloid techniques, precipitation processes, sol-gel processes, etc.

In order to achieve good incorporation of the nanoparticles into the polymer matrix of a polymerizable material for luting of an inlay or of a polymerizable material for increasing the bond strength between luting cement and the hard substance of the tooth, the surfaces of the nanoparticles (preferably of the preferred oxidic nanoparticles) have been organically modified, i.e. the surfaces thereof have organic structural elements. Examples include the surface treatment of the fillers with a silane, which forms silanized nanoparticles. A particularly suitable adhesion promoter in this context is γ-methacryloyloxypropyltrimethoxysilane.

In a further preferred configuration, the nanoscale particles are non-agglomerated, organically surface-modified nanoparticles having a mean particle size less than 200 nm, preferably less than 100 nm, more preferably less than 70 nm, especially in the range from 5 to 60 nm, for example dispersed in a medium, preferably in monodisperse form, these nanoparticles in turn preferably having been silanized.

Constituent C.e and/or D.e: Polymerization Inhibitors

A polymerizable material for luting of an inlay or a polymerizable material for increasing the bond strength between luting cement and the hard substance of the tooth preferably comprises one or more inhibitors, also called stabilizers. These are added to a curable mixture in order to avoid spontaneous polymerization. They react with prematurely formed free radicals, which are scavenged, prevent premature polymerization and increase the storage stability of a polymerizable material for luting of an inlay or a polymerizable material for increasing the bond strength between luting cement and the hard substance of the tooth.

Standard inhibitors are phenol derivatives such as hydroquinone monomethyl ether (HQME) or 2,6-di-tert-butyl-4-methylphenol (BHT). Further inhibitors such as 2,2-diphenyl-1-picrylhydrazyl radicals, galvinoxyl radicals, triphenylmethyl radicals, 2,3,6,6-tetramethylpiperidinyl-1-oxyl radicals (TEMPO), and derivatives of TEMPO or phenothiazine and derivatives of this compound, are described in EP 0 783 880 B1, and these form part of the present application by way of reference. Alternative inhibitors are specified in DE 101 19 831 A1 or EP 1 563 821 A1, which form part of the present application by way of reference.

These stabilizers can also be used to regulate the redox initiation.

Constituent D.f: Solvents

A polymerizable material for increasing the bond strength between luting cement and the hard substance of the tooth preferably comprises one or more solvents, preferably in a total amount of 5 to 65% by weight, more preferably in a total amount of 10 to 50% by weight, based in each case on the total mass of the mixture.

A polymerizable material for increasing the bond strength between luting cement and the hard substance of the tooth may comprise water as a solvent.

Also suitable are the organic solvents customarily used, for example hydrocarbons, ketones and esters, for example toluene, xylene, isooctane, acetone, butanone, methyl ethyl ketone, ethyl acetate, butyl acetate, tetrahydrofuran, N-methylpyrrolidone, dimethylacetamide and dimethylformamide. It is also possible to use alcohols such as ethanol, propanols, butanols, pentanols, hexanols, cyclohexanol, heptanols, octanols, nonanols, decanols, etc. Cycloaliphatic or arylaliphatic alcohols are likewise suitable.

In a preferred configuration, a polymerizable material for increasing the bond strength between luting cement and the hard substance of the tooth comprises an organic solvent, preferably selected from the group consisting of water-miscible organic solvents, preferably acetone, ethanol, n-propanol and isopropanol, and mixtures thereof.

More preferably, a polymerizable material for increasing the bond strength between luting cement and the hard substance of the tooth comprises water and at least one water-miscible organic solvent, preferably acetone. In this case, the ratio of acetone to water is preferably in the range from 1:1 to 10:1, more preferably in the range from 2:1 to 8:1, further preferably in the range from 3:1 to 5:1.

Constituent C.f and/or D.g: Additives

A polymerizable material for luting of an inlay or a polymerizable material for increasing the bond strength between luting cement and the hard substance of the tooth may comprise, as component C.f and/or D.g, various additives matched to the end use, activators, coinitiators, pigments, reactive diluents, molecular weight regulators, flow agents, leveling agents, antiskinning agents, defoamers, antistats, plasticizers, lubricants, wetting agents and dispersants, preservatives, for example fungicides and/or biocides, rheology modifiers such as thixotropic agents and/or thickeners, sensitizers, interface-active substances, oxygen scavengers and/or free-radical scavengers, pigments, dyes, light stabilizers, matting agents, flame retardants, release agents, etc.

UV absorbers, which are capable of absorbing UV radiation, for example, through their conjugated double bond systems and aromatic rings, may optionally additionally be a constituent of a polymerizable material for luting of an inlay or of a polymerizable material for increasing the bond strength between luting cement and the hard substance of the tooth. Examples of UV absorbers are 2-hydroxy-4-methoxybenzophenone, phenyl salicylate or 3-(2'-hydroxy-5'-methylphenyl)benzotriazole.

A polymerizable material for luting of the composite inlay in the cavity or a polymerizable material for increasing the bond strength between luting cement and the hard substance of the tooth additionally comprises, as an additive, one or more fluoride-releasing substances, preferably sodium fluoride and/or amine fluorides.

In addition, one or more surfactants may be a constituent of a polymerizable material for luting of an inlay or of a polymerizable material for increasing the bond strength between luting cement and the hard substance of the tooth.

E

If the polymerizable material for increasing the bond strength between luting cement and the hard substance of the tooth is unable to condition the tooth substance, the solution of an acid is additionally first used to condition the hard substance of the tooth.

EXAMPLES

The invention is illustrated in detail by examples hereinafter, but these do not constitute a restriction of the subject matter of the invention.

As examples, a polymerizable material for production of a dental model (example 1a), a polymerizable material for production of an inlay (example 2a), and a non-self-adhesive (example 3) and a self-adhesive (example 4) polymerizable material for luting of the composite inlay were produced as constituents of an inventive kit for indirect chairside production of composite inlays. For comparison, a polymerizable material for production of a dental model (example 1b) and a polymerizable material for production of an inlay (example 2b) were produced, these being unsuitable as constituents of an inventive kit for indirect chairside production of composite inlays.

Unless stated otherwise, all figures are based on weight. The following abbreviations customary in the field are used:
BHT: 2,6-di-tert-butyl-4-methylphenol
Bis-GMA: 2,2-bis[4-(2-hydroxy-3-methacryloyloxypropoxy)phenyl)propane
DABE: ethyl p-N,N-dimethylaminobenzoate
TEDMA: triethylene glycol dimethacrylate
UDMA: 7,7,9-trimethyl-4,13-dioxo-5,12-diazahexadecane 1,16-dioxydimethacrylate Example 1: Polymerizable Material for Production of a Dental Model

| Base paste | | 1a | 1b |
| --- | --- | --- | --- |
| A.a.5 | Additive: Ethynylcyclohexanol | 0.175 | 0.04 |
| A.a.2 | Si—H-functionalized polydimethylsiloxane (Si—H content: 7.8 mmol/g) | 14.52 | 10.98 |
| A.a.2 | Si—H-functionalized polydimethylsiloxane (Si—H content: 3.0 mmol/g) | | 4.57 |
| A.a.1 | Vinyl-functionalized polydimethylsiloxane (Vinyl content: 1.40 mmol/g; viscosity: 3000-5000 mPas) | 5.83 | 5.05 |

-continued

| | | 1a | 1b |
|---|---|---|---|
| A.a.1 | Vinyl-functionalized polydimethylsiloxane (Vinyl content: 0.05 mmol/g; viscosity: 10 000 mPas) | 1.71 | 0.00 |
| A.a.1 | Vinyl-functionalized polydimethylsiloxane (Vinyl content: 0.2 mmol/g; viscosity: 9000 mPas) | 0.00 | 10.04 |
| A.a.1 | Vinyl-functionalized polydimethylsiloxane (Vinyl content: 0.3 mmol/g; viscosity: 200 mPas) | 14.27 | 31.92 |
| A.a.4 | Fumed silanized silica (primary particle size = 6 nm) | 2.73 | 9.94 |
| A.a.4 | Silanized cristobalite flour ($d_{50}$ =30 µm) | 58.20 | 27.46 |
| A.a.5 | Additive: Color paste | 0.99 | 0.00 |
| | Catalyst paste | 1a | 1b |
| A.a.3 | Platinum concentrate (Karstedt catalyst in polydimethylsiloxane (Pt content 2%)) | 0.46 | 0.26 |
| A.a.1 | Vinyl-functionalized polydimethylsiloxane (Vinyl content: 1.40 mmol/g; viscosity: 3000-5000 mPas) | 6.15 | 4.56 |
| A.a.1 | Vinyl-functionalized polydimethylsiloxane (Vinyl content: 0.05 mmol/g; viscosity: 10 000 mPas) | 1.81 | 0.00 |
| A.a.1 | Vinyl-functionalized polydimethylsiloxane (Vinyl content: 0.03 mmol/g; viscosity: 65 000 mPas) | 0 | 9.12 |
| A.a.1 | Vinyl-functionalized polydimethylsiloxane (Vinyl content: 0.3 mmol/g; viscosity: 200 mPas) | 29.14 | 38.19 |
| A.a.1 | Vinyl-functionalized polydimethylsiloxane (Vinyl content: 0.2 mmol/g; viscosity: 9000 mPas) | 0 | 10 |
| A.a.4 | Fumed silanized silica (primary particle size = 6 nm) | 2.71 | 10.21 |
| A.a.4 | Silanized cristobalite flour ($d_{50}$ = 30 µm) | 58.74 | 27.66 |
| A.a.5 | Additive: Color paste | 0.99 | 0 |

The respective constituents of the base and catalyst pastes were homogenized by intimate mixing with a double planetary mixer and then degassed under reduced pressure. The material was then dispensed free of air bubbles into 2K cartridges (50 ml, 1:1, from Mixpac). For the measurements, the cartridge was inserted into a suitable dispenser and a mixing cannula (MB 3.2 16 S) was used for automatic mixing of the material in the correct mixing ratio of 1:1 when it was pressed out.

The processing time was measured at 23° C. (50% rel. air humidity) by discharging a strip of the model silicone of length 15 cm onto a mixing block. Subsequently, a spatula was used every 5 seconds to check whether the viscosity of the material had altered. The time until significant change in the viscosity was noted as the processing time.

The setting time was determined in an oscillating measurement with a Rheometer Physica MCR 301 (Anton Paar GmbH, Graz, Austria). For this purpose, the polymerizable material for production of a dental model to be examined was applied directly from the cartridge to the measurement plate of a plate/plate system (D=25 mm, gap=1 mm), and the rise in viscosity caused by setting was recorded at 30° C. and at a frequency of f=4 Hz and a deformation of γ=1%. The setting time has been attained when the magnitude of the complex viscosity (|η*|) viscosity reaches a plateau value. The setting times (from commencement of mixing) of the polymerizable materials of examples 1a and 1b were 5 min.

The measurement of deformation under pressure was performed to ISO 4823 (elastomeric impression materials). The specimen was demolded 2:30 min after commencement of mixing; the measurement was started after 3 min.

For the material from example 1a, a processing time of 60 seconds and a deformation under pressure of 0.68% were determined, and for the material from example 1b likewise a processing time of 60 seconds and a deformation under pressure of 6.17%.

Example 2: Polymerizable Material for Production of an Inlay

| | Constituents | 2a % by wt. | 2b % by wt. |
|---|---|---|---|
| B.a.2 | First microparticle fraction: silanized dental glass $d_{50}$ = 3.5 µm | 49.43 | 0.0 |
| B.a.2 | Second microparticle fraction: silanized dental glass $d_{50}$ = 1.0 µm | 16.47 | 68.2 |
| B.a.1 | Non-agglomerated surface-modified nanoscale $SiO_2$ particles ($d_{50}$ = 50 nm) | 23.0 | 0.00 |
| B.a.1 | Fumed silanized silica (primary particle size = 6 nm) | 0.00 | 5.4 |
| B.b.1 | Methacrylate 1: bis-GMA | 4.3 | 11.1 |
| B.b.1 | Methacrylate 2: UDMA | 3.1 | 11.1 |
| B.b.2 | Methacrylate 3: TEDMA | 3.1 | 3.1 |
| B.c | Initiators: DABE, camphorquinone | 0.65 | 0.65 |
| B.d | Additives: Color pigments, stabilizers | ad 100 | ad 100 |

Monomers 1, 2 and 3, and initiators and additives, were first homogenized in a plastic vessel by means of a precision glass stirrer. Subsequently, the fillers were added and a homogenous paste was produced by intimate mixing with a double planetary mixer and the mixture was degassed under reduced pressure.

The polymerization volume shrinkage (polymerization shrinkage) was determined by the bonded-disc method (Dental Materials 2004, 20, 88-95). 100 mg of material were exposed for a period of 40 seconds (soft start) (Celalux II, VOCO GmbH Cuxhaven), and the polymerization shrinkage was measured over a period of 1800 seconds.

The flexural strength was determined in accordance with standard ISO 4049 on a material testing machine from Zwick. The measurements reported are each the mean values from five individual measurements.

For the composite from example 2a, a polymerization shrinkage of 1.6% and a flexural strength of 183 MPa were determined. For the composite from example 2b, the values were 2.5% and 154 MPa.

Example 3: Polymerizable Material for Luting of an Inlay

| | Base paste constituents | % by wt. |
|---|---|---|
| C.a.1 | First microparticle fraction: silanized dental glass $d_{50}$ = 1.0 µm | 13.8 |
| C.a.1 | Second microparticle fraction: silanized dental glass $d_{50}$ = 3.5 µm | 42.5 |
| C.a.1 | Third microparticle fraction: silanized dental glass $d_{50}$ = 8 µm | 14.2 |
| C.a.2 | Fumed silanized silica (primary particle size = 6 nm) | 2.8 |
| C.b | Methacrylate 1: bis-GMA | 13.0 |
| C.b | Methacrylate 2: TEDMA | 12.9 |
| C.c | Initiators: Camphorquinone, DABE, N,N-dihydroxyethyl-p-toluidine | 0.797 |
| C.e | Polymerization inhibitors: BHT | 0.003 |

-continued

| Catalyst paste constituents | | % by wt. |
|---|---|---|
| C.a.1 | First microparticle fraction: silanized dental glass $d_{50}$ = 0.7 µm | 25.9 |
| C.a.1 | Second microparticle fraction: silanized dental glass $d_{50}$ = 3.0 µm | 42.7 |
| C.a.2 | Fumed silanized silica (primary particle size = 6 nm) | 2.5 |
| C.b | Methacrylate 1: bis-GMA | 13.8 |
| C.b | Methacrylate 2: TEDMA | 13.8 |
| C.c | Initiators: Dibenzoyl peroxide | 0.18 |
| C.e | Polymerization inhibitors: BHT | 0.05 |
| C.f | Additives: Color pigments | ad 100 |

The monomers, and also initiators and additives, were first homogenized in a plastic vessel by means of a precision glass stirrer. Subsequently, the fillers were added and the mixture was mixed with a double planetary mixer. Subsequently, the paste was homogenized with a three-roll mill and degassed with a double planetary mixer under reduced pressure.

Example 4: Polymerizable Self-Adhesive Material for Luting of an Inlay

| Base paste constituents | | % by wt. |
|---|---|---|
| C.a.1 | First microparticle fraction: silanized dental glass $d_{50}$ = 1.5 µm | 4.0 |
| C.a.1 | Second microparticle fraction: silanized dental glass $d_{50}$ = 3.0 µm | 53.8 |
| C.a.2 | Fumed silanized silica (primary particle size = 12 nm) | 8.0 |
| C.b | Methacrylate 1: Ethoxylated bisphenol A dimethacrylate | 6.2 |
| C.b | Methacrylate 2: UDMA | 7.1 |
| C.b | Methacrylate 3: Hexanediol dimethacrylate | 10.2 |
| C.b | Methacrylate 4: TEDMA | 6.6 |
| C.c | Initiators: Camphorquinone, DABE, N,N-dihydroxyethyl-p-toluidine | 0.94 |
| C.e | Polymerization inhibitors: BHT | 0.09 |
| C.f | Additives: Color pigments | ad 100 |

| Catalyst paste constituents | | % by wt. |
|---|---|---|
| C.a.1 | First microparticle fraction: silanized dental glass $d_{50}$ = 1.5 µm | 5.7 |
| C.a.1 | Second microparticle fraction: silanized dental glass $d_{50}$ = 3.0 µm | 58.1 |
| C.a.2 | Fumed silanized silica (primary particle size = 12 nm) | 2.2 |
| C.b | Methacrylate 1: bis-GMA | 3.3 |
| C.b | Methacrylate 2: UDMA | 11.2 |
| C.b | Methacrylate 3: Ethylene glycol dimethacrylate | 8.9 |
| C.d | Adhesion monomer glyceryl dimethacrylate phosphate | 9.5 |
| C.c | Initiators: Dibenzoyl peroxide | 0.5 |
| C.f | Additives: Color pigments | ad 100 |

The monomers, and also initiators and additives, were first homogenized in a plastic vessel by means of a precision glass stirrer. Subsequently, the fillers were added and mixed with a double planetary mixer. Subsequently, the paste was homogenized with a three-roll mill and degassed with a double planetary mixer under reduced pressure.

Measurement Method for Determination of the Adhesion Values

To determine the adhesion properties of the luting cements from examples 3 and 4, the adhesion values were determined analogously to ISO CD 29022 (=VOCO test method) on the composites from examples 2a and 2b.

For the determination of the bond strength of the luting cements on the composite from example 2a and example 2b, specimens were produced therefrom with a diameter of 15 mm and a height of 4 mm and light-cured for 40 s (Celalux II, VOCO GmbH Cuxhaven). Subsequently, a silicone ring was placed on. The luting cement from example 3 or 4 was introduced into the opening of the silicone ring and light-cured for 40 s (cylindrical test specimen (3 mm (height)×5 mm (diameter) (Celalux, VOCO GmbH Cuxhaven)). The finished samples were stored at 37° C. and 100% relative air humidity in a sample cabinet. After 24 h, the shear bond strength was determined with the aid of a universal testing machine (1 mm/min). After the measurement, the exact dimensions of the test specimen for the calculation of the adhesion (reported in MPa) were determined with a micrometer.

The following adhesion values were determined:

| | Bond strength [MPa] |
|---|---|
| Polymerizable material for luting of an inlay from example 3 on composite from example 2a | 19 |
| Polymerizable material for luting of an inlay from example 4 on composite from example 2a | 21 |
| Polymerizable material for luting of an inlay from example 3 on composite from example 2b | 3 |
| Polymerizable material for luting of an inlay from example 4 on composite from example 2b | 6 |

In further studies, the fitting accuracy of the inlays produced using the components described as constituents of an inventive kit and the comparative examples specified was also examined.

In freshly extracted human molars, three-surface (mesial-occlusal-distal) inlay cavities were first prepared. Impressions were subsequently taken of these with an alginate (Blueprint® Xcreme, from Dentsply DeTrey, Konstanz). The impression obtained was then cast with a polymerizable material for production of a dental model. After the polymerizable material had set, the dental model was removed. Through layer-by-layer introduction of a polymerizable material for production of an inlay and subsequent photopolymerization (20 seconds per layer, Celalux II, VOCO GmbH Cuxhaven) of the respective layer, a composite inlay was obtained. This was wiped twice with isopropanol and dried with oil-free compressed air. Subsequently, it was inserted into the tooth cavity to check for size and then cleaned again with water and isopropanol and dried with oil-free compressed air. If a non-self-adhesive polymerizable material for luting of an inlay has been used, Futurabond DC (batch No. 1151482, VOCO GmbH Cuxhaven) was first introduced into the cavity according to the instructions in the user information as a polymerizable material for increasing the bond strength between polymerizable material for luting of an inlay and the hard substance of the tooth, and photopolymerized. If the polymerizable material for luting of an inlay used subsequently was self-adhesive, this step was not needed. In the next step, a polymerizable material for luting of an inlay was applied to the previously produced and non-pretreated, i.e. non-sand-blasted, non-silanized, non-etched, non-primed and non-roughened, composite inlay, and the composite inlay was inserted directly into the tooth cavity and pressed in gently. Excess polymerizable material for luting of an inlay which escapes at the cavity margins was removed cautiously, and then the curing of the luting cement was awaited. To complete the restoration, it was finally polished with a polisher (Dimanto, Voco GmbH Cuxhaven, 8000 rpm).

The teeth were then subjected to thermal cycling stress (THE1200 Thermocycler, SD Mechatronik, Feldkirchen-Westerham, 3000 cycles, 30 s at 5° C., 12 s dripping time, 30 s at 55° C., 12 s dripping time). After removal from the Thermocycler, the restored teeth were stored in a 2% methylene blue solution at 37° C. for 24 hours and then embedded into an epoxy material (Scandiplex, Scan-DIA Hagen). The embedded teeth were then sawn through from mesial through occlusal to distal (Well 3241, well Diamantdrahtsagen GmbH, Mannheim, A 3.3 diamond saw, diameter 0.30 mm). The two sections of each tooth were examined with a light microscope (Wild M3C, Leica Wetzlar, 40-fold magnification), and firstly the thickness of the cement layer was determined, and secondly the marginal integrity was categorized subjectively on the basis of the depth of any color penetration.

When the polymerizable materials described in examples 1-4 were used, the following results were achieved:

| Polymerizable material used for production of a dental model | Polymerizable material used for production of a composite inlay | Layer thickness of the polymerizable material for luting of a composite inlay from example 4 | Assessment of marginal integrity |
|---|---|---|---|
| Example 1a | Example 2a | 15 µm | No color penetration evident |
| Example 1a | Example 2b | 75 µm | Color penetration shows clear marginal gap |
| Example 1b | Example 2a | Composite inlay was too large to be bonded into the cavity | |
| Example 1b | Example 2b | | |

The tests described in table 2 were likewise conducted using the material from example 3 rather than the polymerizable material for luting of an inlay from example 4. In this case, as described above, Futurabond DC was additionally used as polymerizable material for increasing the bond strength between the polymerizable material for luting of an inlay and the hard substance of the tooth. The results correspond to the results from table 2. In the case of use of a polymerizable material for production of a dental model with excessively high deformation under pressure (example 1b), the inlays produced were too large to be able to be bonded into the cavity without further processing. A polymerizable material for production of a composite inlay with excessively large polymerization shrinkage (example 2b), in contrast, led to an excessively large bond joint and, as a result of this, to poorer marginal integrity.

The invention claimed is:
1. A kit for restoration of a tooth cavity, comprising
   A. a polymerizable material for production of a dental model, comprising either
      A.a. addition-crosslinking silicones or
      A.b. cationically curable polyethers,
   B. a polymerizable material for production of a composite inlay, comprising
      B.a. a total amount of fillers in the range from more than 75 to 95% by weight, based on the total mass of the polymerizable material for production of a composite inlay B,
      B.b. a total amount of polymerizable monomers or monomer mixtures in the range from 3 to less than 25% by weight, based on the total mass of the polymerizable material for production of a composite inlay B, wherein the total amount of polymerizable monomers is selected from the group consisting of carbosilanes, monomers which cure via ring-opening metathesis polymerization, and dental (meth)acrylate monomers, and
      B.c. one or more photoinitiator(s) and/or initiator(s) for chemical curing,
      and
   C. a polymerizable material for luting of a composite inlay in the cavity, comprising
      C.a. a total amount of fillers of more than 40 to 80% by weight based on the total mass of the polymerizable material for luting of a composite inlay in the cavity C,
      C.b. 16.8 to less than 60% by weight of a total amount of one, two or more polymerizable monomers, based on the total mass of the polymerizable material for luting of a composite inlay in the cavity C, the one, two or more polymerizable monomers being selected from the group consisting of carbosilanes, monomers which cure via ring-opening metathesis polymerization, and dental (meth)acrylate monomers,
      C.c. 0.1 to 10% by weight of one or more photoinitiator(s) and/or initiator(s) for chemical curing, based on the total mass of the polymerizable material for luting of a composite inlay in the cavity C,
      C.e. polymerization inhibitors, and
      C.f. less than 3% by weight of additives, based on the total mass of the polymerizable material, for luting of a composite inlay in the cavity C,
   wherein the composite inlay which has not been sandblasted, nor silanized, nor etched, nor primed, nor roughened, before being bonded into the tooth cavity and is obtainable by curing the polymerizable material for production of a composite inlay B. has fully polymerized surfaces, and the deformation under pressure of the polymerizable material for production of a dental model A., measured to ISO 4823, is not more than 3.5%, and the polymerizable material for production of a dental model A has a Shore D hardness, determined to DIN 53505, of between 25 and 85, and the polymerization shrinkage of the polymerizable material for production of a composite inlay B., measured by the bonded-disc method, is not more than 2.0%, and wherein the adhesive force between the composite inlay and the luting cement, measured by the VOCO test method, is at least 8 MPa.

2. The kit for restoration of a tooth cavity according to claim 1, wherein
   A.a. comprises
      A.a.1. 10-40% by weight of polysiloxanes comprising polyatomic crosslinkable groups,
      A.a.2. 2-10% by weight of organo-hydropolysiloxanes,
      A.a.3. 0.01-1% by weight of catalyst, and
      A.a.4. 50-90% by weight of fillers,
      wherein the percentages by weight are based on the total mass of the addition-crosslinking silicones,
   or
   A.b. comprises
      A.b.1. 30-90% by weight of aziridine group-bearing copolymers, A.b.2. 1-10% by weight of starter substances suitable for bringing about the curing of the aziridine group-bearing copolymers,
A.b.3. 3-45% by weight of fillers,
A.b.4. 2-85% by weight of additives,
wherein the percentages by weight are based on the total mass of the cationically curable polyethers, and B.a. comprises
B.a.1. a total amount in the range from 2 to 30% by weight of organically surface-modified nanoparticles having a mean primary particle size less than 200 nm and
B.a.2. a total amount in the range from 45 to less than 85% by weight of microparticles having a mean particle size in the range from 0.4 µm to 10 µm,
wherein the percentages by weight for components B.a.1 and B.a.2 are based on the total mass of the polymerizable material for production of a composite inlay B, and C.a. comprises
C.a.1. one or more fractions of microparticles having a mean particle size of 0.4 µm to 10 µm,
C.a.2. nanoscale, solid particles having a primary particle size of not more than 200 nm.

3. The kit for restoration of a tooth cavity according to claim 2,
wherein, from the polymerizable material for production of a dental model A., component A.a.1 comprises a mixture of two linear vinylmethylsiloxanes, wherein the dynamic viscosity, measured to DIN 53018 at 25° C., of one linear vinylmethylsiloxane having terminal vinyl groups is in the range from 200 mPas up to and including 2500 mPas (low-viscosity vinylmethylsiloxane), and that of the second linear vinylmethylsiloxane likewise having terminal vinyl groups is within the range from greater than 2500 mPas up to and including 65000 mPas (high-viscosity vinylmethylsiloxane), and wherein the weight ratio of the low-viscosity to the high-viscosity vinylmethylsiloxane is 6:1 to 1:4,
wherein component A.a.2 has two to three Si—H bonds per molecule,
wherein component A.a.3 is a platinum catalyst,
wherein component A.a.4 is selected from the group consisting of cristobalite, silicates, montmorillonites, bentonites, metal oxide powders, titanium dioxide, gypsum, inorganic salts, glass, crystalline and amorphous silica, quartz, diatomaceous earth, and nanoscale particles in the form of non-aggregated and non-agglomerated particles,
wherein the fillers are in surface-treated form,
wherein the addition-crosslinking silicone A.a is a two-component system composed of base paste and catalyst paste,
wherein base paste and catalyst paste are present in a volume ratio of 10:1 to 1:10 and
wherein A.a has a processing time at 23° C. of more than 30 seconds, and a setting time at 30° C. of less than 7 minutes.

4. The kit for restoration of a tooth cavity according to claim 2, wherein the polymerizable material for production of a composite inlay B comprises component B.a.1 to an extent of more than 8% by weight to 30% by weight of organically surface-modified nanoparticles having a mean primary particle size less than 100 nm, and component B.a.2 to an extent of more than 65 to less than 85% by weight of microparticles having a mean particle size of 0.4 µm to 10 µm, wherein the percentages by weight are based on the total mass of the polymerizable material for production of a composite inlay B.

5. The kit for restoration of a tooth cavity according to claim 4, wherein the microparticles of component B.a.2 have a multimodal particle size distribution.

6. The kit for restoration of a tooth cavity according to claim 2, wherein A.a further comprises: A.a.5 additives,
wherein component A.a.5 comprises
one or more inhibitor(s) in amounts of 0.001-0.15% by weight, based on the total mass of component A.a,
one or more stabilizer(s) in amounts of 0.1 to 5% by weight, based on the total mass of component A.a, and
one or more rheology modifiers in amounts of 1 to 10% by weight, based on the total mass of component A.a.

7. The kit for restoration of a tooth cavity according to claim 1, wherein the dental (meth)acrylates of the polymerizable material for production of a composite inlay B are selected from the groups of
B.b.1 comprising one, two or more monomers selected from the group consisting of 2,2-bis[4-(2-hydroxy-3-(meth)acryloyloxypropoxy)phenyl)propane (bisGMA), bisphenol A glycidyl (meth)acrylate, bisphenol B glycidyl (meth)acrylate, bisphenol C glycidyl (meth)acrylate, bisphenol F glycidyl (meth)acrylate, alkoxylated bisphenol A glycidyl (meth)acrylate, alkoxylated bisphenol A di(meth)acrylate, 7,7,9-trimethyl-4,13-dioxo-5,12-diazahexadecane 1,16-dioxydi(meth)acrylate (UDMA), compounds which are free-radically polymerizable via (meth)acrylate groups and comprise a polyalicyclic structural element, and ormocers and
B.b.2 comprising one, two or more further free-radically polymerizable monomer(s) selected from the group consisting of (meth)acrylates which are not part of the list described for B.b.1, and
wherein the ratio of the mass of components B.b.1 to the mass of components B.b.2 is in the range from 10:1 to 1:10.

8. The kit for restoration of a tooth cavity according to claim 7, wherein the one, two or more further free-radically polymerizable monomers selected from the group consisting of (meth)acrylates of components B.b.2 are selected from the group consisting of ethylene glycol di(meth)acrylate (EGDMA), 1,6-hexanediol di(meth)-acrylate (HEDMA), triethylene glycol di(meth)acrylate (TEDMA), 1,12-dodecanediol di(meth)acrylate (DODMA), decanediol di(meth)-acrylate, polyethylene glycol di(meth)acrylate (PEGDMA), butanediol di(meth)acrylate, tetraethylene glycol di(meth)acrylate, neopentyl glycol di(meth)acrylate, 2-hydroxypropyl 1,3-di(meth)acrylate, 3-hydroxypropyl 1,2-di(meth)-acrylate, pentaerythrityl di(meth)acrylate, glyceryl di(meth)acrylate, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)-acrylate, 2,3-dihydroxypropyl (meth)acrylate, 2-hydroxypropyl 1,3-di(meth)acrylate and 3-hydroxypropyl 1,2-di (meth)acrylate, 2-(meth)-acryloyloxyethyl dihydrogenphosphate, bis[2-(meth)acryloyloxyethyl] hydrogenphosphate, 2-(meth)acryloyloxyethylphenyl hydrogenphosphate, 6-(meth)acryloyloxyhexyl dihydrogenphosphate, 10-(meth)acryloyloxydecyl dihydrogenphosphate (MDP), 1,3-di(meth)acryloyloxypropane 2-dihydrogenphosphate, 1,3-di(meth)acryloyloxypropane 2-phenyl hydrogenphosphate and bis[5-(2-(meth)acryloyloxyethoxycarbonyl)heptyl] hydrogenphosphate, 4-(meth)acryloyloxyethyltrimellitic acid (4-MET), 4-(meth)acryloyloxyethyltrimellitic anhydride (4-META), 4-(meth)acryloyloxydecyltrimellitic acid, 4-(meth)acryloyloxydecyltrimellitic anhydride, 11-(meth)acryloyloxy-1,1-undecanedicarboxylic acid, 1,4-di(meth)acryloyloxypyromellitic acid, 2-(meth)acryloyloxyethylmaleic acid, 2-(meth)acryloyloxyethylphthalic acid and 2-(meth)acryloyloxyethylhexahydrophthalic acid, and polymerizable phosphoric esters bearing a polyalicyclic structural element.

9. The kit for restoration of a tooth cavity according to claim 1, wherein the deformation under pressure of the polymerizable material for production of a dental model A, measured to ISO 4823, is not more than 1.5%, and the polymerization shrinkage of the polymerizable material for production of a composite inlay B, measured by the bonded-disc method, is not more than 1.8%.

10. The kit for restoration of a tooth cavity according to claim 1, further comprising:
    D. a polymerizable material for establishment of a bond between the hard substance of the tooth and luting cement, comprising
        D.a. one or more adhesion monomer(s) containing a phosphoric acid radical, a diphosphoric acid radical, a phosphonic acid radical, a thiophosphoric acid radical or a sulfonic acid radical,
        D.b. monomers copolymerizable with component D.a. other than component D.a.,
        D.c. one or more fillers,
        D.d. one or more photoinitiator(s) and/or initiator(s) for chemical curing, and
        D.e. polymerization inhibitors.

11. The kit for restoration of a tooth cavity according to claim 1, further comprising
    E. an acid solution for etching the hard substance of the tooth.

12. The kit for restoration of a tooth cavity according to claim 1, wherein the polymerizable material for luting of a composite inlay in the cavity C. further comprises:
    C.d. one or more adhesion monomer(s) other than component C.b. for luting of the composite inlay in the cavity, wherein the component C.d. adhesion monomer(s) comprises a phosphoric acid radical, a diphosphoric acid radical, a phosphonic acid radical, a thiophosphoric acid radical or a sulfonic acid radical in a proportion of less than 35% by weight, based on the total mass of the polymerizable material for luting of a composite inlay in the cavity C.

13. A method for production of a composite inlay, the method comprising the following steps:
    casting an impression of a tooth cavity with a first polymerizable material for production of a dental model A,
    polymerizing the first polymerizable material to produce the dental model A,
    applying a second polymerizable material for production of a composite inlay B, to the dental model, formed by the first polymerized material,
    forming the second polymerizable material, into the form of an inlay which fills the tooth cavity of which an impression has been taken,
    polymerizing the second polymerizable material to produce the composite inlay B,
    withdrawing the polymerized composite inlay B produced from the dental model A,
    removing the inhibited or incompletely polymerized second polymerizable material from the composite inlay B by wiping-off and application of alcohol or alcoholic or aqueous disinfection solutions;
    wherein the first polymerizable material for production of a dental model A comprises either:
    A.a.) addition-crosslinking silicones, or
    A.b.) cationically curable polyethers; and
    wherein the deformation under pressure of said first polymerizable material, measured to ISO 4823, is not more than 3.5%, and wherein the first polymerizable material has a Shore D hardness, determined to DIN 53505, of between 25 and 85;
    wherein the second polymerizable material for production of a composite inlay B comprises:
    B.a.) a total amount of fillers in the range from more than 75 to 95% by weight, based on the total mass of the second polymerizable material,
    B.b.) a total amount of polymerizable monomers or monomer mixtures in the range from 3 to less than 25% by weight, based on the total mass of the second polymerizable material, wherein the total amount of polymerizable monomers is selected from the group consisting of carbosilanes, monomers which cure via ring-opening metathesis polymerization, and dental (meth)acrylate monomers, and
    B.c.) one or more photoinitiator(s) and/or initiator(s) for chemical curing;
    wherein the polymerization shrinkage of the second polymerizable material as measured by the bonded-disc method is not more than 2.0%, and
    wherein the composite inlay B has fully polymerized surfaces and has not been sand-blasted, nor silanized, nor etched, nor primed, nor roughened.

14. The method for production of a composite inlay according to claim 13,
    wherein the first polymerizable material comprises either
        A.a. addition-crosslinking silicones comprising
            A.a.1. 10-40% by weight of polysiloxanes comprising polyatomic crosslinkable groups,
            A.a.2. 2-10% by weight of organo-hydropolysiloxanes,
            A.a.3. 0.01-1% by weight of catalyst, and
            A.a.4. 50-90% by weight of fillers
            wherein the percentages by weight are based on the total mass of the addition-crosslinking silicones,
        or
        A.b. cationically curable polyethers comprising
            A.b.1. 30-90% by weight of aziridine group-bearing copolymers,
            A.b.2. 1-10% by weight of starter substances suitable for bringing about the curing of the aziridine group-bearing copolymers,
            A.b.3. 3-45% by weight of fillers, and
            A.b.4. 2-85% by weight of additives,
            wherein the percentages by weight are based on the total mass of the cationically curable polyethers, and
            wherein component A.a.4 is selected from the group consisting of cristobalite, silicates, montmorillonites, bentonites, metal oxide powders, titanium dioxide, gypsum, inorganic salts, glass, crystalline and amorphous silica, quartz, diatomaceous earth, and nanoscale particles in the form of non-aggregated and non-agglomerated particles,
            wherein the addition-crosslinking silicone A.a is a two-component system composed of base paste and catalyst paste,
            wherein base paste and catalyst paste are present in a volume ratio of 10:1 to 1:10 and wherein A.a has a processing time at 23° C. of more than 30 seconds, and a setting time at 30° C. of less than 7 minutes, and wherein the deformation under pressure of the addition-crosslinked silicone A.a measured to ISO 4823 is not more than 3.5% and the Shore D hardness, determined to DIN 53505, is in the range between 25 and 85, and wherein the second polymerizable material comprises B.a. a total amount of fillers in the range from more than 75 to 95% by weight, based on the total mass of the second polymerizable material, wherein the total amount of fillers is a mixture of fillers comprising B.a.1. a total amount in the range from 2 to 30% by weight of organically surface-modified nanoparticles having a mean primary particle size less than 200 nm and B.a.2. a total amount in the range from 45 to less than 85% by weight of microparticles having a mean particle size in the range from 0.4 µm to 10 µm, wherein the percentages by weight for components B.a.1 and B.a.2 are based on the total mass of the second polymerizable material, and wherein the microparticles of component B.a.2 are selected from the group consisting of materials based on silicon dioxide, zirconium dioxide and/or titanium dioxide, and also mixed oxides, fumed silicas or precipitated silicas, quartz glass ceramics or dental glass powders, barium glasses or strontium glasses, fluoride ion-releasing glasses, oxides of aluminum or silicon, zeolites, apatites, zirconium silicates, sparingly soluble metal salts and X-ray-opaque fillers, and wherein the organically surface-modified nanoparticles of component B.a.1 are oxides or mixed oxides selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof, wherein the surface-modified nanoparticles are silanized, and B.b. a total amount of polymerizable monomers or monomer mixtures in the range from 3 to 25% by weight is present, based on the total mass of the second polymerizable material, wherein the total amount of polymerizable monomer is selected from the group consisting of carbosilanes, monomers which cure via ring-opening metathesis polymerization, and dental (meth)acrylate monomers, wherein the dental (meth)acrylate monomers in the second polymerizable material are selected from the group consisting of B.b.1 comprising one, two or more monomers selected from the group consisting of 2,2-bis[4-(2-hydroxy-3-(meth)acryloyloxypropoxy)phenyl] propane (bis-GMA), bisphenol A glycidyl (meth) acrylate, bisphenol B glycidyl (meth)acrylate, bisphenol C glycidyl (meth)acrylate, bisphenol F glycidyl (meth)acrylate, ethoxylated bisphenol A glycidyl (meth)acrylate, alkoxylated bisphenol A di(meth)acrylate, 7,7,9-trimethyl-4,13-dioxo-5,12-diazahexadecane 1,16-dioxydi(meth)acrylate (UDMA), compounds which are free-radically polymerizable via (meth)acrylate groups and comprise a polyalicyclic structural element, and ormocers and B.b.2 comprising one, two or more further free-radically polymerizable monomer(s) selected from the group consisting of (meth)acrylates which are not part of the list described for B.b.1, and wherein B.b.2 is selected from the group consisting of ethylene glycol di(meth)acrylate (EGDMA), 1,6-hexanediol di(meth)acrylate (HEDMA), triethylene glycol di(meth)acrylate (TEDMA), 1,12-dodecanediol di(meth)acrylate (DODMA), polyethylene glycol di(meth)acrylate (PEGDMA), butanediol di(meth)acrylate, tetraethylene glycol di(meth)acrylate, neopentyl glycol di(meth)acrylate, 2-hydroxypropyl 1,3-di(meth) acrylate, 3-hydroxypropyl 1,2-di(meth)acrylate, pentaerythrityl di(meth)acrylate, glyceryl di(meth)acrylate, 2-hydroxyethyl (meth)acrylate, 2-hydroxypropyl (meth)-acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxy-propyl 1,3-di(meth)acrylate and 3-hydroxypropyl 1,2-di (meth)acrylate, 2-(meth)acryloyloxyethyl dihydrogenphosphate, bis[2-(meth)acryloyloxyethyl] hydrogenphosphate, 2-(meth)acryloyloxy-ethylphenyl hydrogenphosphate, 6-(meth)-acryloyloxyhexyl dihydrogenphosphate, 10-(meth)acryloyloxydecyl dihydrogenphosphate (MDP), 1,3-di (meth)acryloyloxypropane 2-dihydrogenphosphate, 1,3-di(meth)acryloyloxypropane 2-phenyl hydrogenphosphate and bis [5-(2-(meth)acryloyloxyethoxycarbonyl)heptyl] hydrogenphosphate, 4-(meth)acryloyloxy-ethyltrimellitic acid (4-MET), 4-(meth)acryloyloxyethyltrimellitic anhydride (4-META), 4-(meth)acryloyloxy-decyltrimellitic acid, 4-(meth)acryloyl-oxydecyltrimellitic anhydride, 11-(meth) acryloyloxy-1,1-undecanedi-carboxylic acid, 1,4-di(meth)acryloyl-oxypyromellitic acid, 2-(meth) acryloyl-oxyethylmaleic acid, 2-(meth) acryloyloxy-ethylphthalic acid and 2-(meth) acryloyl-oxyethylhexahydrophthalic acid, and polymerizable phosphoric esters bearing a polyalicyclic structural element, and wherein the ratio of the mass of component B.b.1 to the mass of component B.b.2 is in the range from 10:1 to 1:10, and B.c. one or more photoinitiators and/or initiators for chemical curing, wherein the photoinitiators are selected from the group consisting of alpha-diketones, benzoin alkyl ethers, thioxanthones, benzophenones, acylphosphine oxides, acetophenones, ketals, titanocenes, sensitizing dyes and borate salts, and the initiators of chemical curing are selected from the group consisting of peroxides, barbituric acids, barbituric acid derivatives, salts of barbituric acid, salts of a barbituric acid derivative, malonyl-sulfamides and sulfur compounds in the +2 or +4 oxidation state, and wherein the photoinitiators are used individually or in mixtures, and the photoinitiators used individually or in mixtures are used in combination with accelerators, wherein the accelerators provided are amines, aldehydes, sulfur compounds, barbituric acids and tin compounds, and
  wherein the chemical catalysts are used in combination with redox partners,
   B.d. selected from the group consisting of inhibitors, fluoride-releasing substances, UV absorbers, dyes and flavorings,
wherein the inhibitors are selected from the group consisting of hydroquinone monomethyl ether, phenols, phenothiazine, derivatives of phenothiazine, 2,3,6,6-tetramethylpiperidinyl-1-oxyl radicals, triphenylmethyl radicals, galvinoxyl radicals, 2,2-diphenyl-1-picrylhydrazyl radicals, tert-butylhydroxyanisole and 2,6-di-tert-butyl-4-methylphenol, and
wherein the inhibited or incompletely polymerized second polymerizable material is removed from the composite inlay B by wiping-off and application of alcohols, and/or by application of aqueous/alcoholic solutions.

15. The method for production of a composite inlay according to claim 14, wherein component A.a.1 comprises a mixture of two linear vinylmethylsiloxanes, wherein the dynamic viscosity, measured to DIN 53018 at 25° C., of one linear vinylmethylsiloxane having terminal vinyl groups is in the range from 200 mPas up to and including 2500 mPas (low-viscosity vinylmethylsiloxane), and that of the second linear vinylmethylsiloxane likewise having terminal vinyl groups is within the range from greater than 2500 mPas up to and including 65000 mPas (high-viscosity vinylmethylsiloxane), and
  wherein the weight ratio of the low-viscosity to the high-viscosity vinylmethylsiloxane is 6:1 to 1:4.

16. The method for production of a composite inlay according to claim 14, wherein A.a further comprises: A.a.5 additives,
  wherein component A.a.5 comprises
    one or more inhibitor(s) in amounts of 0.001-0.15% by weight, based on the total mass of component A.a,
    one or more stabilizer(s) in amounts of 0.1 to 5% by weight, based on the total mass of component A.a, and
    one or more rheology modifiers in amounts of 1 to 10% by weight, based on the total mass of component A.a.

17. The method for production of a composite inlay according to claim 14, wherein component A.a.2 has two to three Si—H bonds per molecule, and component A.a.3 is a platinum catalyst.

18. The method for production of a composite inlay according to claim 14, wherein component B.a. further comprises:
  B.a.3. fillers other than B.a.1 and B.a.2, wherein the fillers of component B.a.3 are selected from the group consisting of fibers, finely divided chip 30 polymers, and bead polymers.

19. The method for production of a composite inlay according to claim 14, wherein the chemical catalysts are used in combination with accelerators;
  wherein the photoinitiators are used together with the catalysts of chemical curing;
  wherein the photoinitiator consists of a combination of camphorquinone/amine or of one or more phosphine oxides or of the combination of camphorquinone/amine/phosphine oxides, and the chemical catalyst consists of a combination of peroxide/amine or of the barbituric acid/barbituric acid derivative/salt of barbituric acid/salt of a barbituric acid derivative system and one or more heavy metal salt(s) and/or heavy metal complexes,
  wherein the heavy metal salt of the barbituric acid/barbituric acid derivative/salt of barbituric acid/salt of a barbituric acid derivative system is selected from the group consisting of iron salt, copper salt or cobalt salt and copper acetylacetonate or the bis(1-phenylpentane-1,3-dionato)copper(II) complex,
  wherein the barbituric acid/barbituric acid derivative/salt of barbituric acid/salt of a barbituric acid derivative system additionally comprises ionically bonded halogens or pseudohalogens, and
  wherein a peroxy compound as an oxidizing agent is added to the barbituric acid/barbituric acid derivative/salt of barbituric acid/salt of a barbituric acid derivative system.

20. The method for production of a composite inlay according to claim 13, further comprising repeating the application, forming and polymerizing of the second polymerizable material, when the inlay is to be built up layer by layer.

* * * * *